United States Patent
Colin et al.

(10) Patent No.: US 11,314,846 B1
(45) Date of Patent: Apr. 26, 2022

(54) SURGICAL COMMUNICATION AND COMPUTERIZATION INFRASTRUCTURE

(71) Applicant: OR Link, Inc., Lexington, KY (US)

(72) Inventors: Wayne Colin, Lexington, KY (US); Rick Baker, Lexington, KY (US)

( * ) Notice: Subject to any disclaimer, the term of this patent is extended or adjusted under 35 U.S.C. 154(b) by 1156 days.

(21) Appl. No.: 15/719,261

(22) Filed: Sep. 28, 2017

Related U.S. Application Data

(60) Provisional application No. 62/401,696, filed on Sep. 29, 2016.

(51) Int. Cl.
*G16H 40/40* (2018.01)
*G06F 19/00* (2018.01)
*G16H 10/60* (2018.01)
*G16H 15/00* (2018.01)

(52) U.S. Cl.
CPC ......... *G06F 19/3418* (2013.01); *G16H 10/60* (2018.01); *G16H 40/40* (2018.01); *G16H 15/00* (2018.01)

(58) Field of Classification Search
CPC .............................................. G06Q 50/22–24
See application file for complete search history.

(56) References Cited

U.S. PATENT DOCUMENTS

| | | | |
|---|---|---|---|
| 10,410,746 B2 * | 9/2019 | Moctezuma de la Barrera | A61B 17/154 |
| 2010/0211897 A1 * | 8/2010 | Cohen | G09B 19/00 715/764 |
| 2014/0267658 A1 * | 9/2014 | Speier | H04N 7/181 348/72 |
| 2014/0276855 A1 * | 9/2014 | de la Barrera | A61B 17/17 606/87 |
| 2015/0019234 A1 * | 1/2015 | Cooper | G16H 10/60 705/2 |
| 2015/0346954 A1 * | 12/2015 | Parag | G06F 3/04842 715/763 |
| 2016/0379504 A1 * | 12/2016 | Bailey | G16H 40/63 434/219 |
| 2017/0055896 A1 * | 3/2017 | Al-Ali | A61B 5/05 |
| 2017/0109483 A1 * | 4/2017 | Luo | G16H 40/20 |
| 2019/0005848 A1 * | 1/2019 | Garcia Kilroy | A61B 34/10 |

OTHER PUBLICATIONS

Seo. M., et al., "Bi-Directional Attention Flow for Machine Comprehension," arXIV.org, arXiv:1611.01603v6 [cs.CL], submitted Nov. 5, 2016, 13 pgs.

Wang, Z., et al., "Multi-Perspective Context Matching for Matching for Machine Comprehension," arXIV.org, arXiv:1612.04211v1 [cs.CL], submitted Dec. 13, 2016, 8 pgs.

\* cited by examiner

*Primary Examiner* — Robert A Sorey
(74) *Attorney, Agent, or Firm* — Frost Brown Todd LLC

(57) ABSTRACT

Various embodiments are described herein that relate to visual tools for specifying the setups and data models preferred by a medical professional (e.g., a surgeon) within an operating room. These visual tools can be incorporated into a system which provides various technical benefits, such as ensuring that users are given access to time sensitive information even when their computer(s) is/are offline. In this way, the disclosed technology can address specific technical issues which arise in the context of surgery, including that many operating rooms have little or no network connectivity which could allow potentially vital information specified using visual tools to be accessed.

13 Claims, 24 Drawing Sheets

FIG. 18A (0123)1234567 | Work

9876543210 | Mobile

Additional Information

Number of Hospital Associations
Select

Bovie Settings
Select

Preferred method of contact
Select

Biolar Settings
Select

Glove Size
12

Other preferences

SAVE

FIG. 18B

SURGICAL COMMUNICATION AND COMPUTERIZATION INFRASTRUCTURE

CROSS REFERENCE TO RELATED APPLICATIONS

This is a non-provisional of, and claims the benefit of, U.S. provisional application 62/401,696, filed on Sep. 29, 2016, the disclosure of which is hereby incorporated by reference in its entirety.

FIELD

Various embodiments concern methods and systems which can be used to improve communication related to, and computerization of, surgical procedures.

BACKGROUND

Surgery is an area where increased computerization for purposes such as communication and data analysis could provide tremendous benefits, but where various technical obstacles have prevented such benefits from being achieved. To illustrate, consider the example of preference cards. Preference cards specify the preferences of a medical professional (e.g., a surgeon) for procedures within an operating room. Preference cards directly affect the efficiency of the operating room and critical patient outcomes of surgical procedures in hospitals across the world. Currently, these preference cards will often be written by hand and stored locally at particular institutions, which can make them difficult to access, time consuming to create, and difficult to update. However, there are technical barriers to the computerization and standardization of such cards. For example, attempting to improve upon handwritten cards by migrating to a cloud based system where digital preference cards are stored remotely could actually make things worse, because network connectivity in hospitals (and particularly in operating rooms) can be extremely spotting, meaning that remotely stored preference cards could become unavailable just when they are needed most (e.g., during an operation when delays can be both extremely costly and potentially fatal). Other challenges posed by the unique nature of the surgical context include the need to maintain a sterile environment, which can limit the utility (or feasibility) of many touch based computer interfaces.

Another example of an area in which computerization could improve surgical practices is in tracking the inventory of items which are present in an operating room. Prior methods have involved manually counting items at the end of a surgical procedure and comparing the count against a pick list to confirm that no tools or disposables (e.g., sponges, towels) had been left inside the patient. However, these approaches are vulnerable to human error, which can result in items being left in a patient. While various object recognition and computer vision technologies could potentially be adapted to improve on intra-surgical inventory tracking, these technologies have not been applied in the surgical context. Accordingly, there is a need for technology which can increase the computerization of surgery and its supporting infrastructure while addressing issues such as ensuring that users are given access to time sensitive information even when their computer(s) is/are offline and/or providing functionality for automatically tracking objects and determining their physical positions using a computer vision system during an operation.

SUMMARY

Disclosed herein are various embodiments of technology which can be used to improve the communication and computerization infrastructure for surgical procedures. As an example, based on this disclosure one of ordinary skill in the art could implement a system comprising a cloud based platform comprising a data coordination program and a set of computing devices which are each configured with a preference application and located remotely from the cloud based platform.

In a system comprising a set of computing devices configured with a preference application, the preference application may configure the computing devices to send login information for their users to the cloud based platform, present preference definition interfaces to their users, send preferences for medical procedures to the cloud based platform, store data received from the cloud based platform as connectivity invariant accessible data in local memory, and present data in response to a request for data which was received as connectivity invariant accessible data from the cloud based platform. In this type of system, it is possible that the preferences for the medical procedure could be specified using the set of preference definition interfaces, and that those preferences could be sent to the cloud based platform along with various metadata. This metadata could include metadata indicating the medical procedure for which those preferences were specified, and the user to whom the set of preference definition interfaces was presented when the preferences were specified for the medical procedure. Additionally, it is also possible that that preference application could configure the computing devices to, based on a request for data received from a cloud based platform as connectivity invariant accessible data, retrieve the data from the cloud based platform in the event a connection to the cloud based platform was available, or retrieve the requested data from local memory in the event a connection to the cloud based platform was not available.

In a system comprising a cloud based platform which comprises a data coordination program, the data coordination program could comprise instructions operable to, when executed, cause a computer used to host the cloud based platform to perform various acts. Such acts could include storing preferences received from computing devices with associated metadata in a central database. Such acts could also include determining information to be made accessible to a user of a computing device during a future time period and sending information determined to be made available to the user during the future time period as connectivity invariant accessible data from the central database.

Other types of implementations are also possible. For example, it is possible that the disclosed technology could be used to implement a method which comprises storing preferences specified for one or more medical procedures in a central database along with associated metadata. Such a method could also include determining information to be made accessible to a user of a remote computing device during a future time period, and sending that information from a central database as connectivity invariant accessible data. The disclosed technology could also be used to implement other types of systems, such as a system comprising a means for allowing definition of preferences for a medical procedure and a means for ensuring availability of time sensitive information regarding the medical procedure for a user even when the user's device is offline.

Other potential implementations of the disclosed technology, along with variations on methods and systems of the type described above, will be immediately apparent to and could be implemented without undue experimentation by those of ordinary skill in the art in light of this disclosure. Accordingly, the above examples of potential ways aspects of the disclosed technology could be implemented should be understood as being illustrative only, and should not be treated as limiting on the scope of protection provided by this document or any other document which claims the benefit of this disclosure.

BRIEF DESCRIPTION OF THE DRAWINGS

Various objects, features, and characteristics will become apparent to those skilled in the art from a study of the Detailed Description in conjunction with the appended claims and drawings, all of which form a part of this specification. While the accompanying drawings include illustrations of various embodiments, the drawings are not intended to limit the claimed subject matter.

FIG. 3 depicts an interface which could be presented to surgeon and used to specify a procedure from a menu of procedures.

FIG. 4 depicts an interface which could be presented to a surgeon to allow him or her to select a procedure for which to create/edit a preference card.

FIG. 5 depicts an interface which could be presented if the user had clicked on the pre-op/anesthesia phase in an editing navigation tool.

FIG. 6 depicts an interface which could be used by a surgeon to specify cart(s) for the procedure corresponding to the preference card he or she was creating/editing.

FIG. 14 depicts an interface which would allow a user to define his or her preferences with respect to trays.

Figure 16:
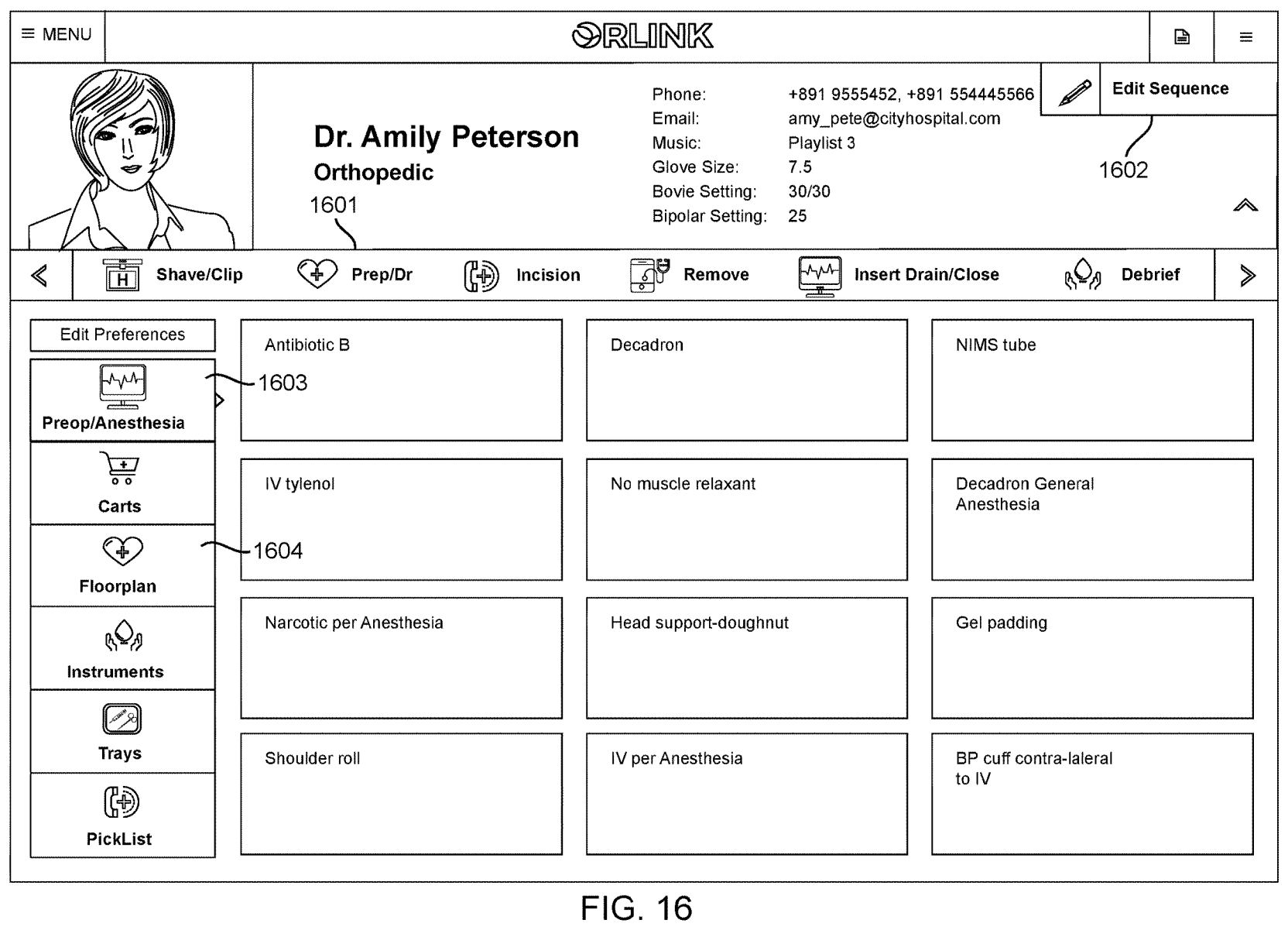

FIG. 16 depicts an interface that could be presented to display a previously created preference card for the fictitious "Dr. Amily Peterson."

Figure 18A:
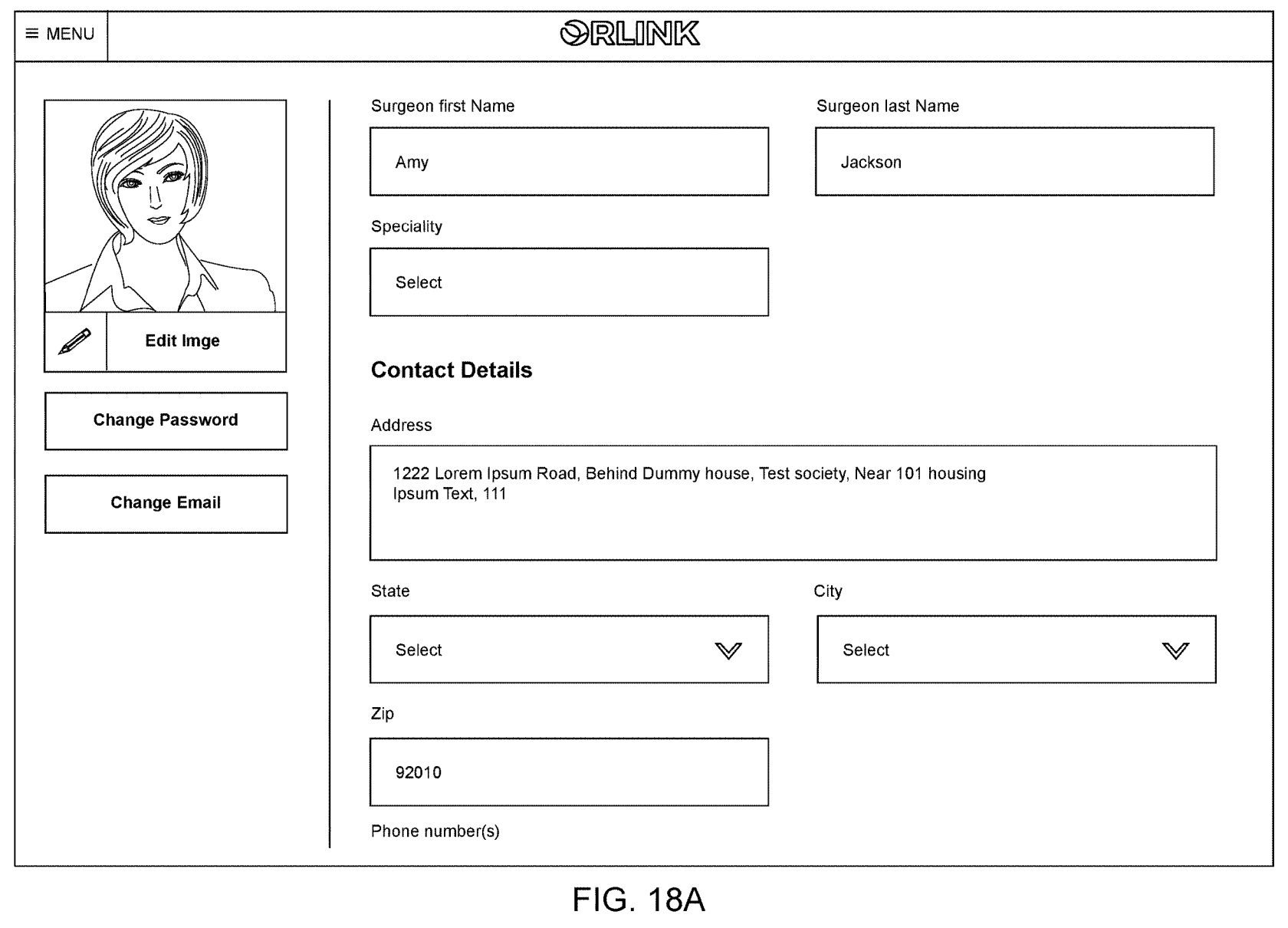

FIGS. 18A and 18B depict, when FIG. 18A is placed vertically above FIG. 18B, an interface which could be used to define preferences for a surgeon which are not specific to any particular medical procedure.

Figure 1:
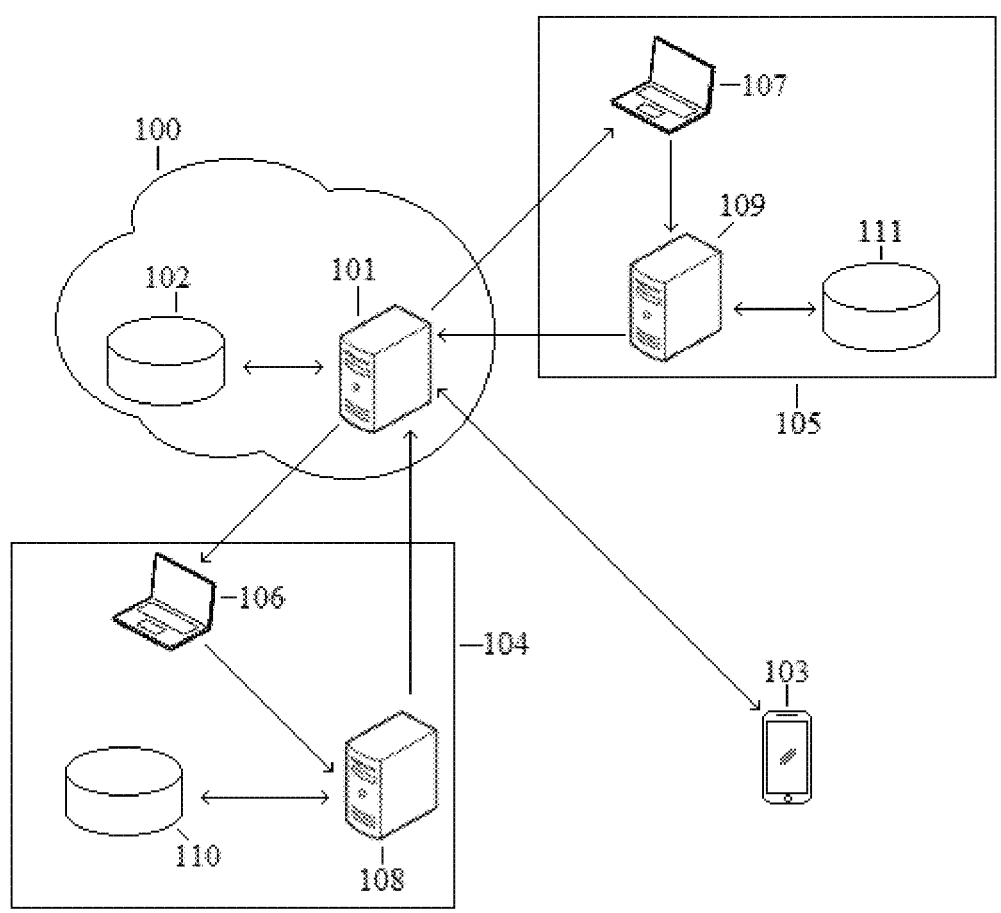
FIG. 1 depicts an environment in which various aspects of the disclosed technology can be deployed.

The figures depict various embodiments described throughout the Detailed Description for the purposes of illustration only. While specific embodiments have been shown by way of example in the drawings and are described in detail below, the invention is amenable to various modifications and alternative forms. The intention is not to limit the invention to the particular embodiments described. Accordingly, the claimed subject matter is intended to cover all modifications, equivalents, and alternatives falling within the scope of the invention.

DETAILED DESCRIPTION

Various embodiments are described herein that can increase the computerization of surgery and its supporting infrastructure while addressing issues such as ensuring that users are given access to time sensitive information even when their computers are offline. These include embodiments which provide visual tools which can be used to specify the preferences of a surgeon for particular types of procedures, such as their preferred setups for an operating room. As described herein, these types of visual tools can be used to organize surgical team resources, the structure of the operating room, and the processes/tasks executed in the operating room in ways that aid in optimizing surgical procedures. This document also describes technology which can be used to gather and analyze data regarding surgical procedures, and which can use that data to improve those procedures, such as by offering proactive suggestions for operating room setups and/or identifying best practices for various procedures. However, it should be understood that, while this disclosure sets forth various specific ways in which the technology can be embodied, and various benefits which it can provide, those embodiments and benefits are intended to be illustrative only, and should not be treated as implying limitations on the protection provided by this document or other document which claims the benefit of, or incorporates, this disclosure.

Turning now to the figures, FIG. 1 depicts an environment in which various aspects of the disclosed technology can be deployed. In that figure, a cloud based platform 100 comprising a server 101 and a database 102 is in communication with a user device 103, such as a tablet or other mobile computing device which could be used by a surgeon or other medical professional. In the environment of FIG. 1, the server 101 of the cloud platform 100 is also in communication with devices at a first hospital 104 and a second hospital 105. These devices could include computers 106 107 used by administrators at the first and second hospitals 104 105, and servers 108 109 at the first and second hospitals 104 105 which could be used to access one or more data stores 110 111 at the hospitals.

In an environment such as shown in FIG. 1, aspects of the disclosed technology can be used to selectively access, replicate and modify data in various locations in a manner which is consistent with security, administrative, privacy and other requirements of the different entities involved. To illustrate, consider the process of creating/editing and publishing an electronic preference card which will be used to specify procedures to be followed when a doctor performs a particular type of operation. Preferably, in preparation for creation of a preference card, an administrator of a hospital would create an account at the cloud platform 100 which would allow a surgeon associated with that hospital to create preference cards for procedures he or she would perform at that hospital. Then, once the surgeon had an account on the cloud platform which was associated with a hospital, he or she would log in 201 with the credentials associated with that hospital (e.g., an email address set up or identified for the surgeon by the administrator of the hospital in question), and specify 202 the procedure (e.g., abdominal thyroidectomy) for which the preference card would be created or edited. Once the procedure had been specified 202, the surgeon could then define his or her preferences for that procedure 203. As is explained in more detail below, this preference definition 203 could include one or more of: defining preop/anesthesia preferences 204, defining cart preferences 205, defining floorplan preferences 206, defining individual instrument preferences 207, defining surgical pack/tray preferences 208 and defining pick list preferences 209, and one or more of those sub-processes process could include selectively combining data from the data store of the relevant hospital with non-hospital specific data from the cloud platform 100.

Figure 2:
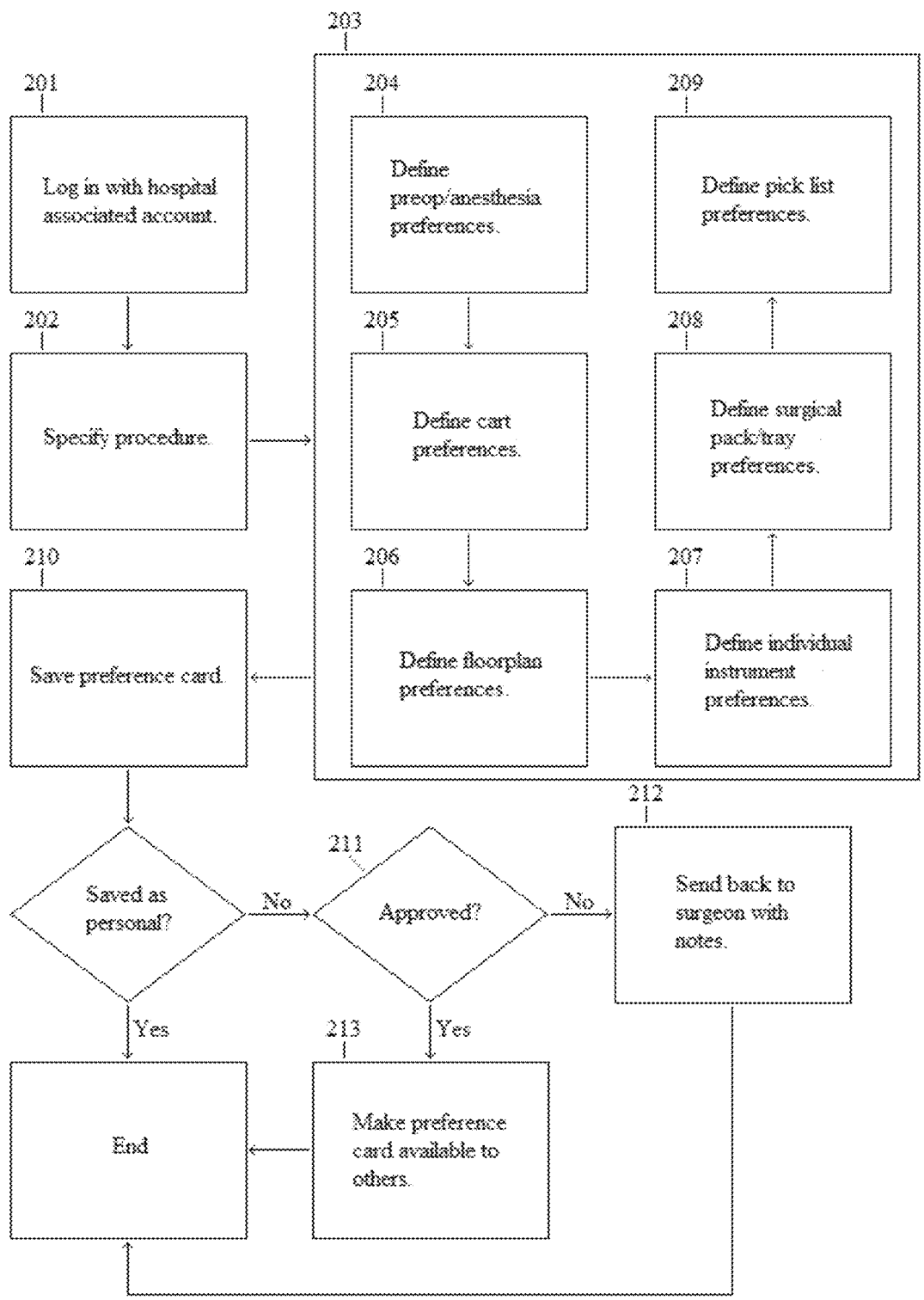
FIG. 2 depicts a process which could be used to create or edit a preference card.

Once the preferences for a procedure had been defined 203, the preference card could be saved 210 in the database 102 of the cloud based platform. As shown in FIG. 2, this saving could be saving 210 the preference card as a personal preference card for the surgeon, in which case the surgeon could return to it at a later time to make any further edits he or she may feel are appropriate (e.g., if the surgeon didn't define all of his or her preferences, he or she could return to the preference definition 203 step and fill in the preferences which had previously been left blank) before it is made available to others. The saving 210 could also be saving the preference card in a manner that indicates it is suitable for being made available to others (e.g., publishing the preference card), in which case it could be subjected to an approval workflow 211 and either sent back to the surgeon 212 with notes (if it is not approved) or (if it is approved) made available to others 213 at the hospital so that they could use it as a record of the preferences of that surgeon when he or she performs the specified procedure at the hospital where the preference card was approved. More information about interfaces and workflows which could be used in some embodiments in connection with the activities illustrated in FIG. 2 is provided below in connection with FIGS. 3-15.

Figure 3:
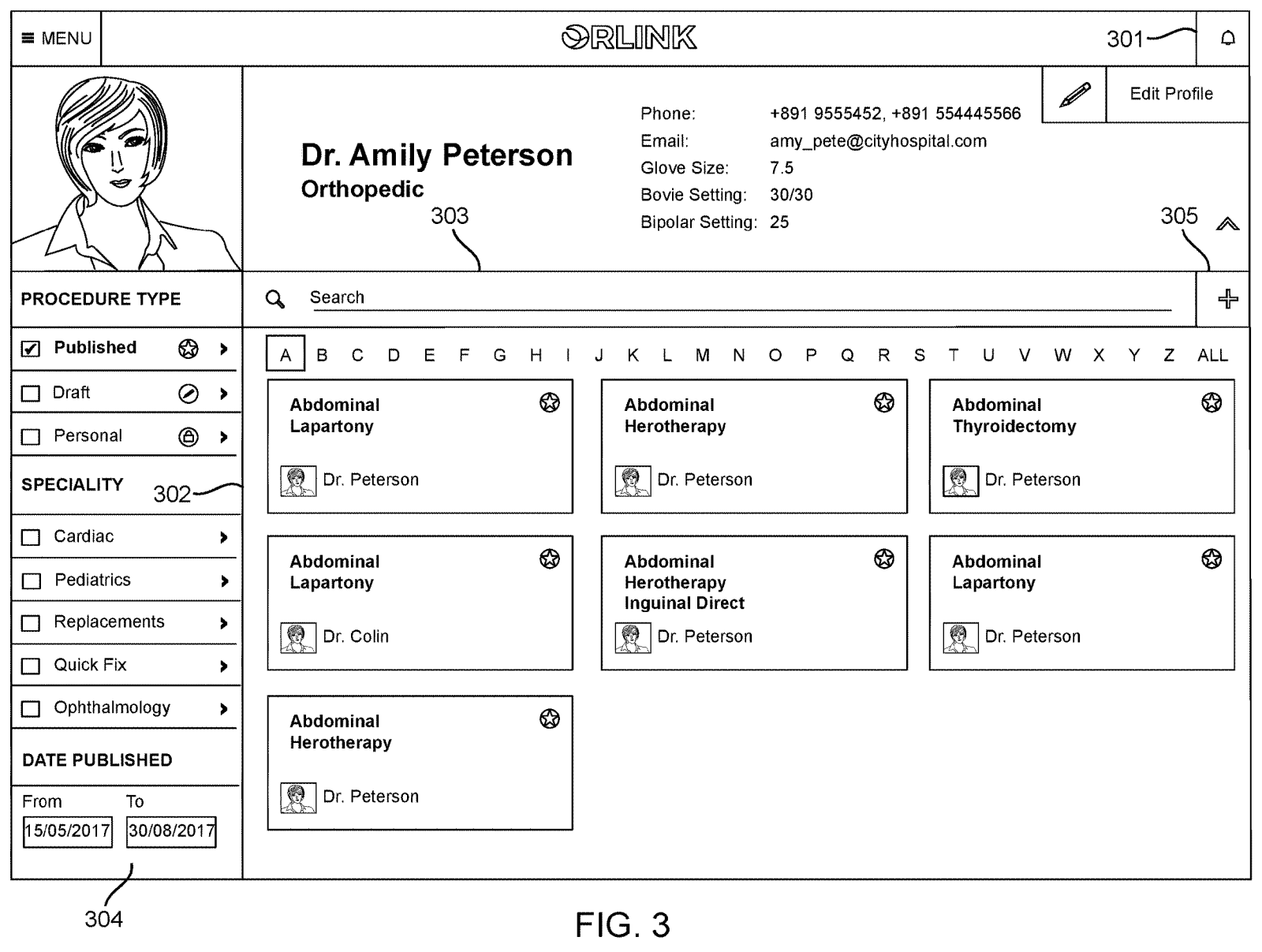

Turning now to FIG. 3, that figure illustrates an interface which could be presented to a surgeon after he or she had logged in 201. In that interface, the surgeon is presented with a modification tool 305 which the surgeon could activate to indicate that he or she wished to edit or create a preference card. The interface of FIG. 3 also presents the surgeon with a notifications tool 301, which could be used to alert the surgeon of messages generated by other users or by the system itself. For example, if one of his or her preference cards had been rejected by a hospital administrator and sent back for further edits, the surgeon could be made aware of this via the notification tool 301. The interface of FIG. 3 also includes a list of procedures 302, which could be selected from by the surgeon to access the corresponding preference cards. In addition to the procedure list 302, the surgeon is also presented with a procedure search tool 303, and a set of filters 304 which he or she could use to narrow down the procedures which would be included in the list 302 so as to simplify selection of the correct procedure.

Figure 4:
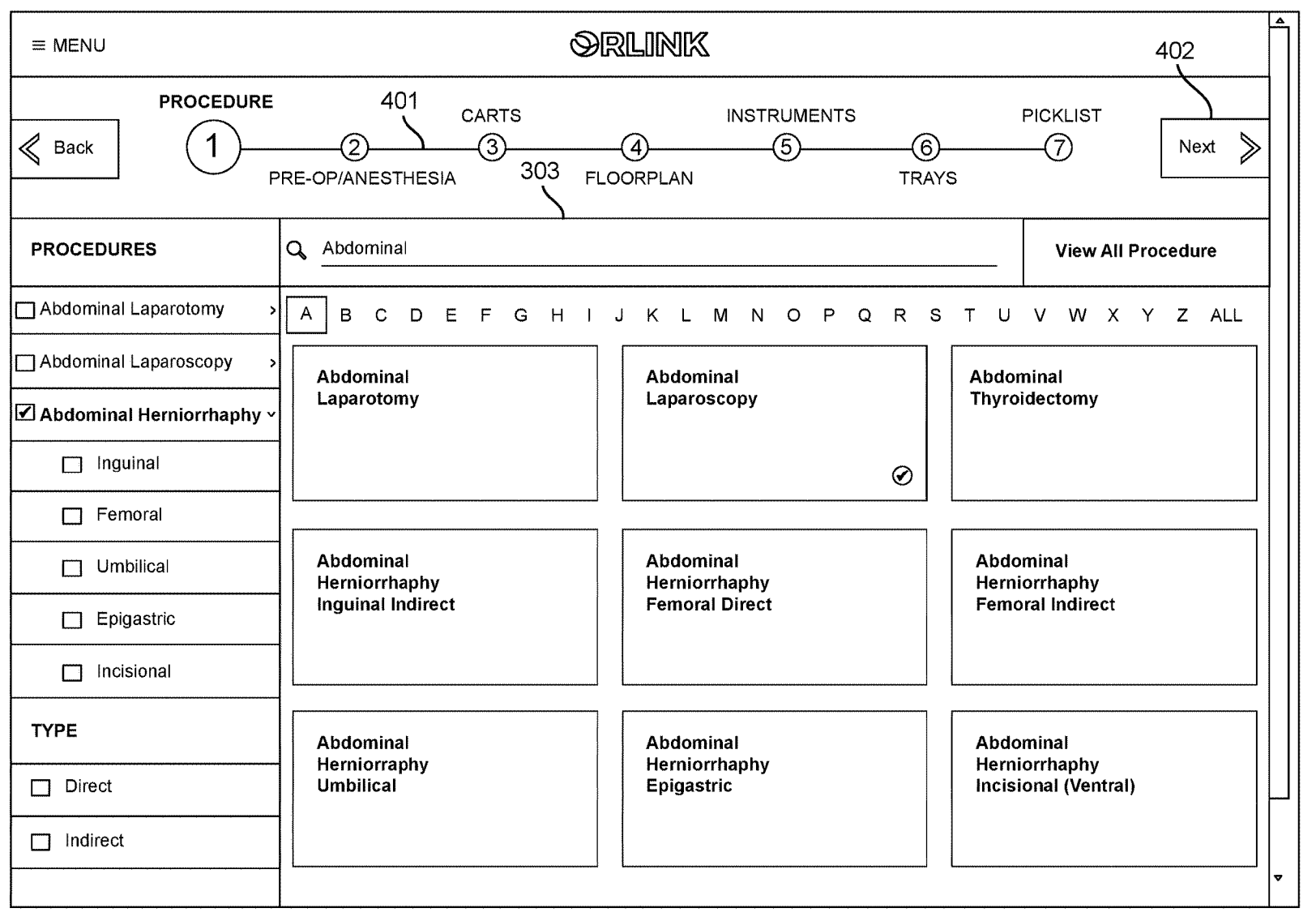
Figure 5:
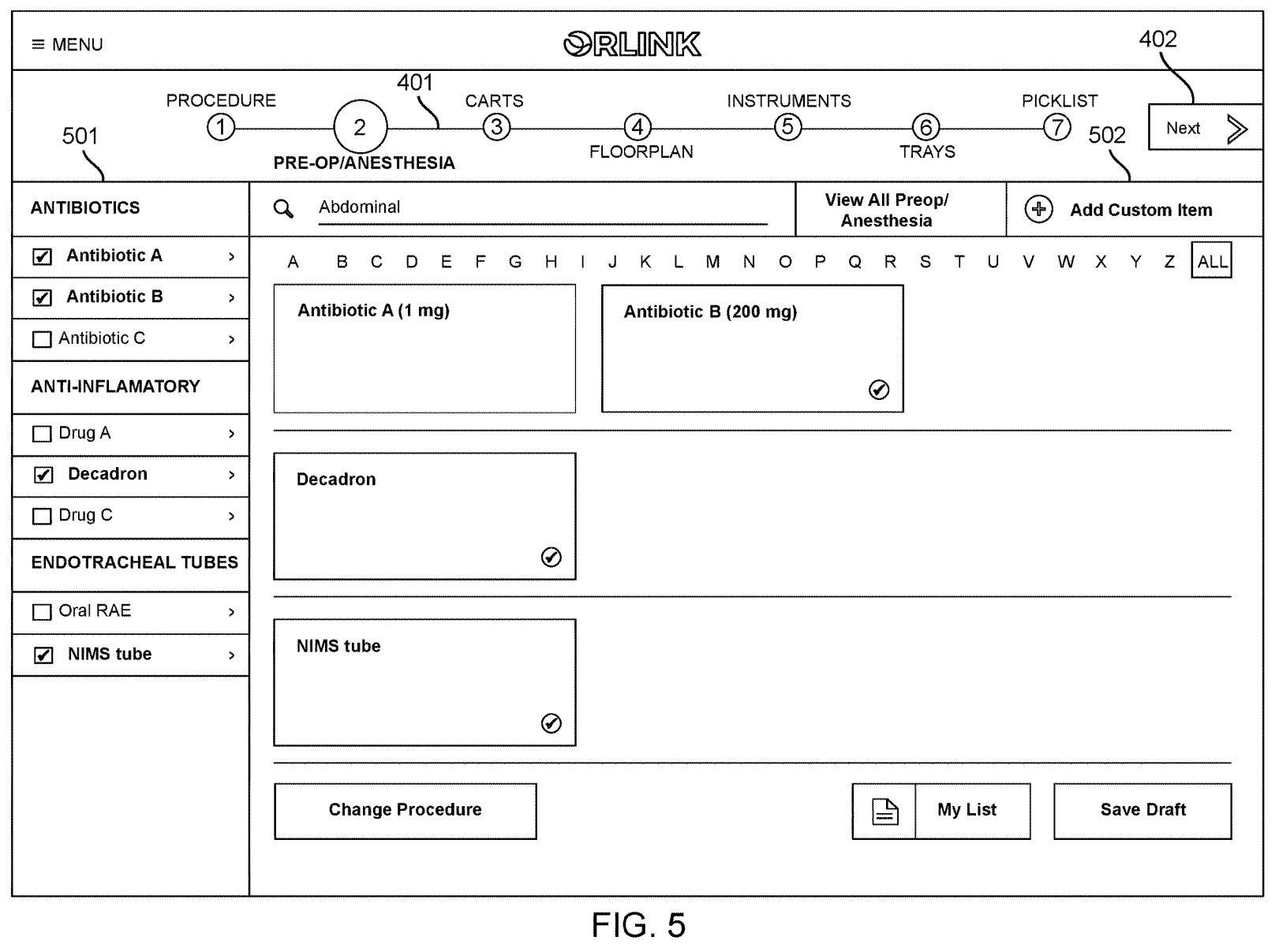

Turning now to FIG. 4, that figure depicts an interface which could be presented to a surgeon to allow him or her to select a procedure for which to create/edit a preference card (e.g., as could be presented to a user after he or she activates the modification tool 305 of FIG. 3). From that interface, the user could use the editing navigation tool 401 to select particular preferences he or she wished to define, or could use the next tool 402 to step through the types of preferences one by one so as to completely define the preference card. FIG. 5 depicts an interface which could be presented if the user had clicked on the pre-op/anesthesia phase in the editing navigation tool 401, or after activating the next tool 402 from the interface of FIG. 4. In the interface of FIG. 5, the user is presented with a list 501 of drugs and tools which could be used during the pre-op/anesthesia phase (e.g., antibiotics, endotracheal tubes, etc.). This list could be created by the server 102 in the cloud platform 100 querying the database at the relevant hospital (either directly or through an administrator computer or hospital server, depending on the level of permissions and access the server 101 of the cloud platform 100 was provided in a particular embodiment) for what tools and drugs which could be used during the pre-op/anesthesia phase were available in that hospital's inventory, and could potentially supplement this using a master list of drugs and tools maintained in the database 102 of the cloud platform 100. Elements could also be added to the list 501 of FIG. 5 through the use of the add custom item control 502 which a surgeon could use to define a new item (e.g., by adding text which would be displayed as a new item when the surgeon accessed the interface of FIG. 5 in the future) if he or she wanted to use a particular tool or drug which was not present in either the hospital's database or the master list of drugs and tools in the database 102 of the cloud platform 100.

Figure 6:
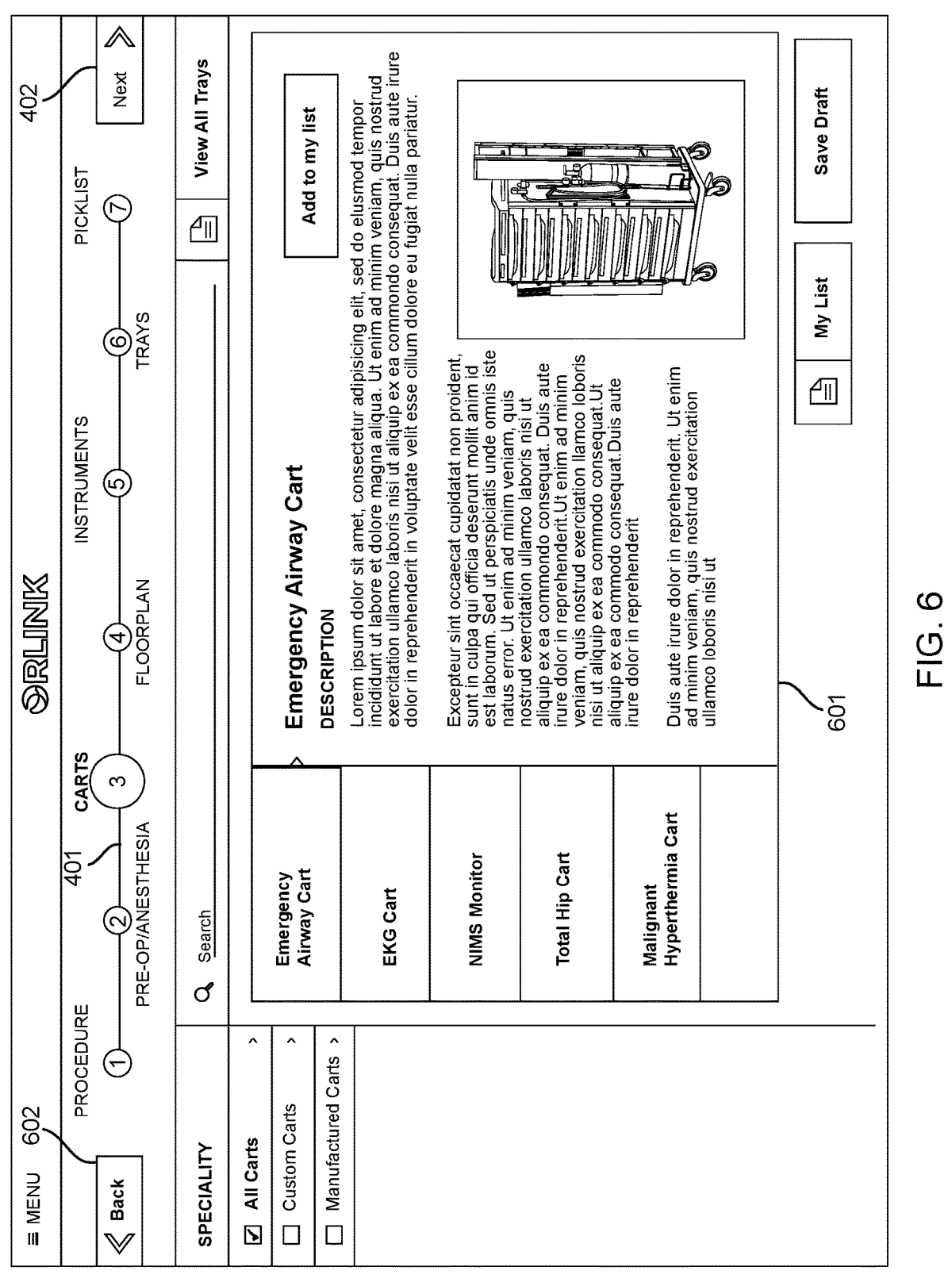

FIG. 6 depicts an interface which could be used by a surgeon to specify cart(s) for the procedure corresponding to the preference card he or she was creating/editing. As will be apparent to one of ordinary skill in the art, the interface of FIG. 6 is broadly similar to that of FIG. 5, and would be used in a similar way, with the surgeon selecting from among available (or potentially available carts) using a list, and being provided with similar navigation tools to those illustrated in FIGS. 4 and 5. In implementations which include interfaces having this type of similarity, it is possible that the similarity could be used to allow simplification of interface creation or display on a user device. For example, when interfaces are presented in a browser based manner or defined using the HTML markup language, preferably inline frames (iFrames) will be used to define the page as a collection of separate documents such that when an individual portion of an interface changes only the document related to that portion would need to be reloaded, thus providing both a more responsive and less bandwidth intensive experience for a user. With that said, the interfaces are not identical. For example, while the interface of FIG. 5 simply listed various tools and drugs which could be used in the prep-op/anesthesia phase, the interface of FIG. 6 includes space 601 for more detailed information about various carts, including descriptive text and pictures of the carts the surgeon may want to have available. FIG. 6 also includes an additional back tool 602 which could be used to sequentially retrace the phases addressed in the preference card, just as the next tool 402 could be used to move through those phases in order.

Figure 7:
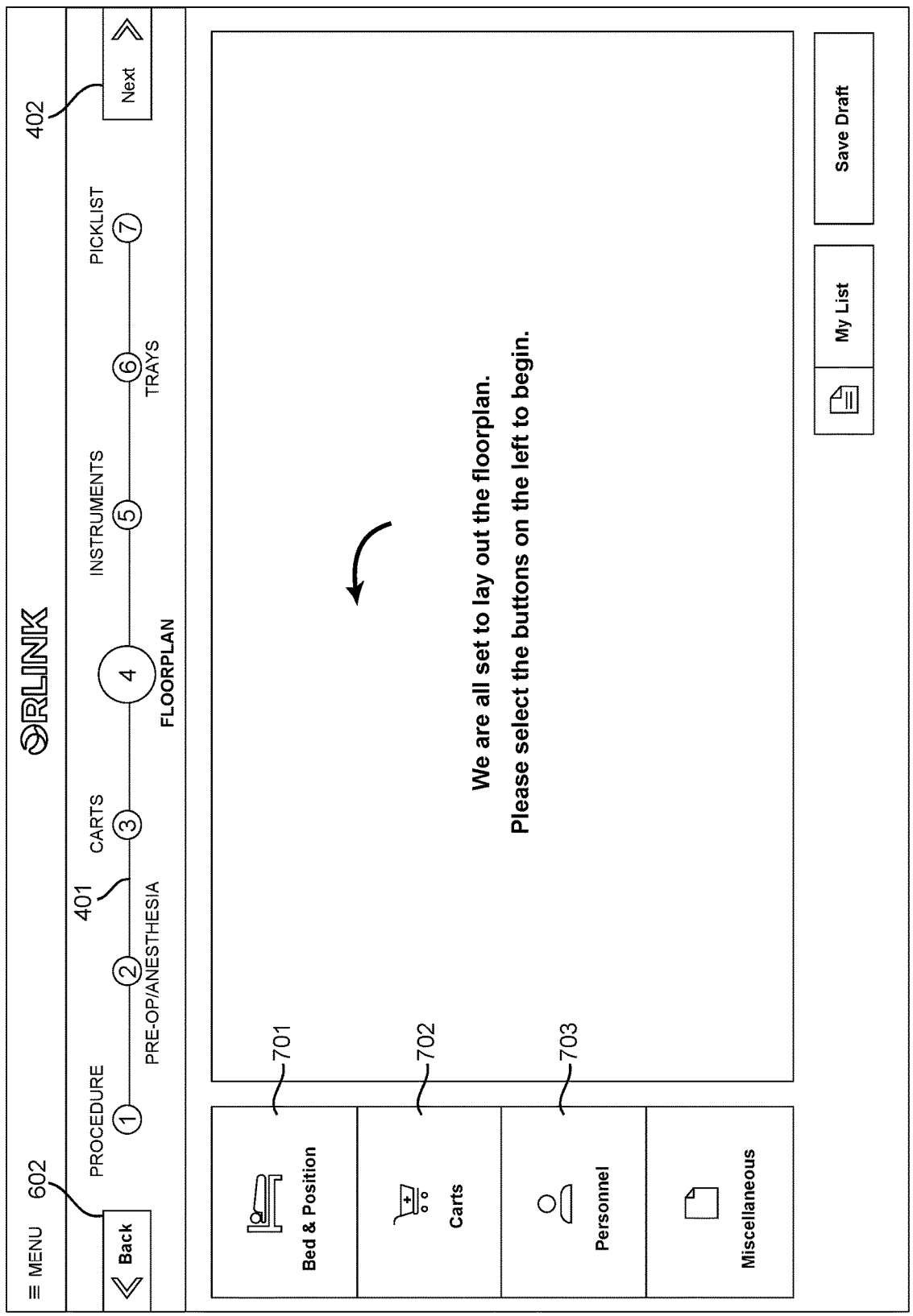
FIG. 7 depicts an interface in which the floorplan is entirely undefined, and presents the user with tools which he or she would use to specify items or personnel that should be present during the procedure.
Figure 8:
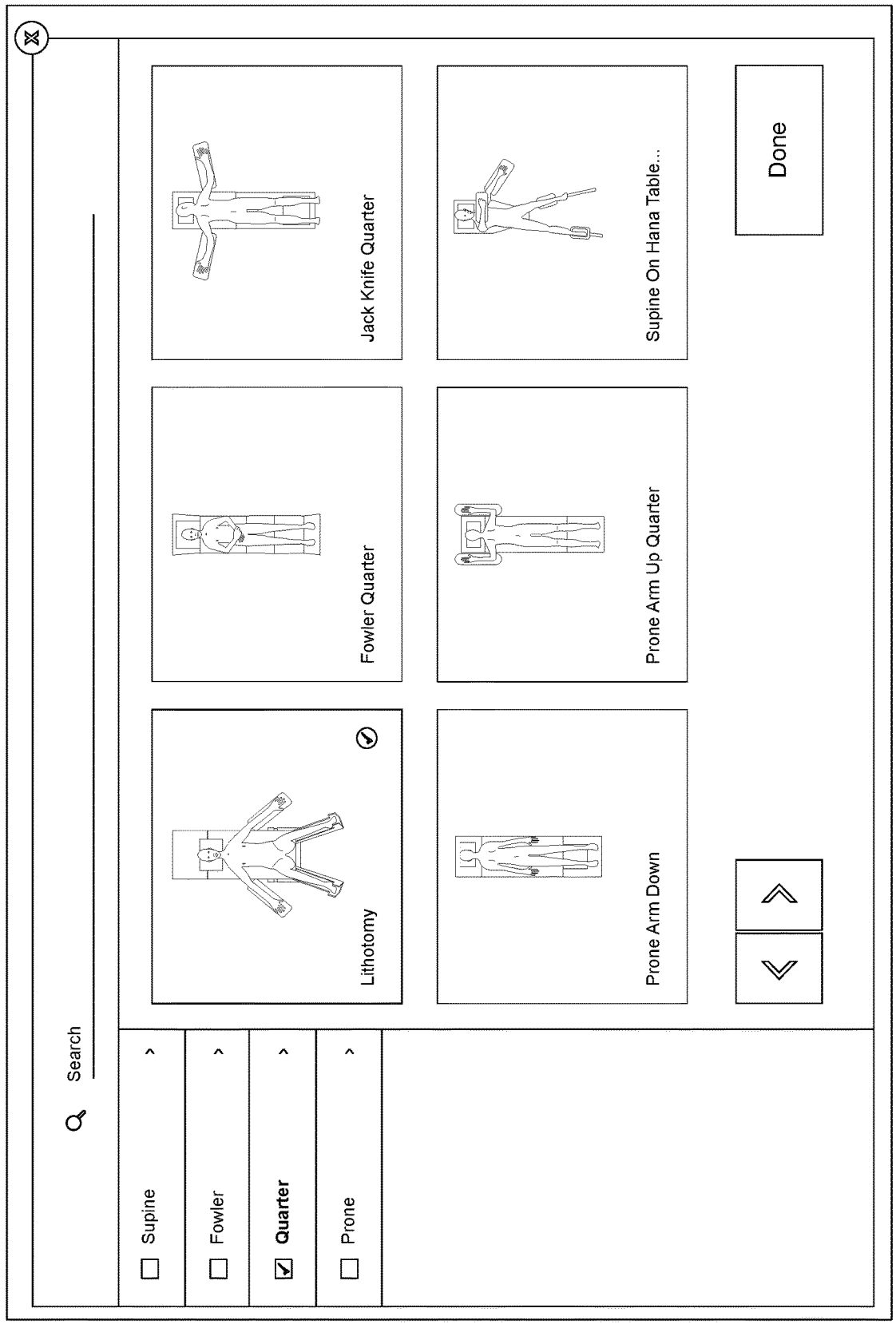
FIG. 8 depicts an interface showing graphical representations of various beds and potential patient positions from which the user could make a selection.
Figure 9:
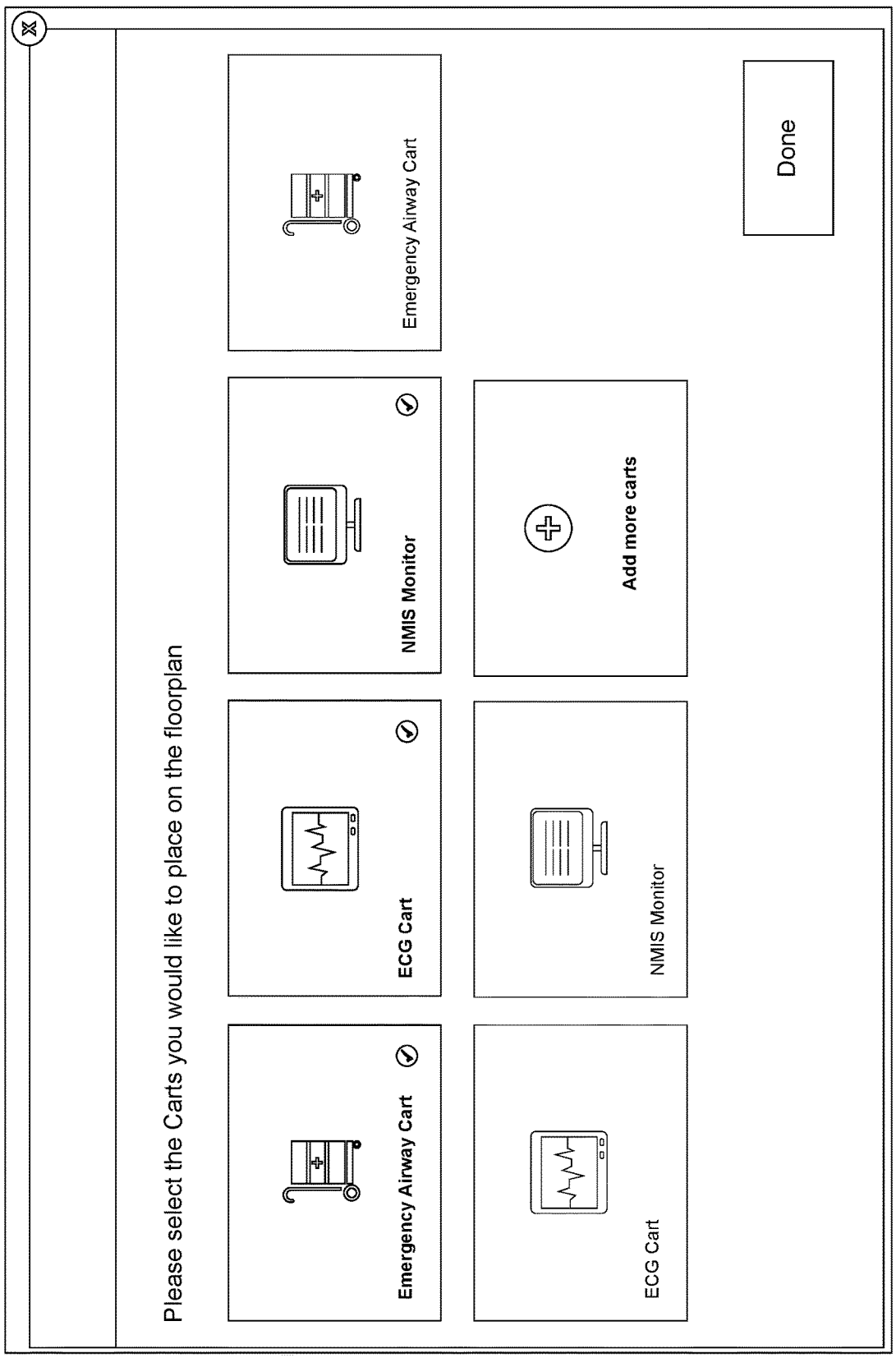
FIG. 9 depicts an interface from which the user could select cart(s) which should be present in the operating room during the procedure.
Figure 10:
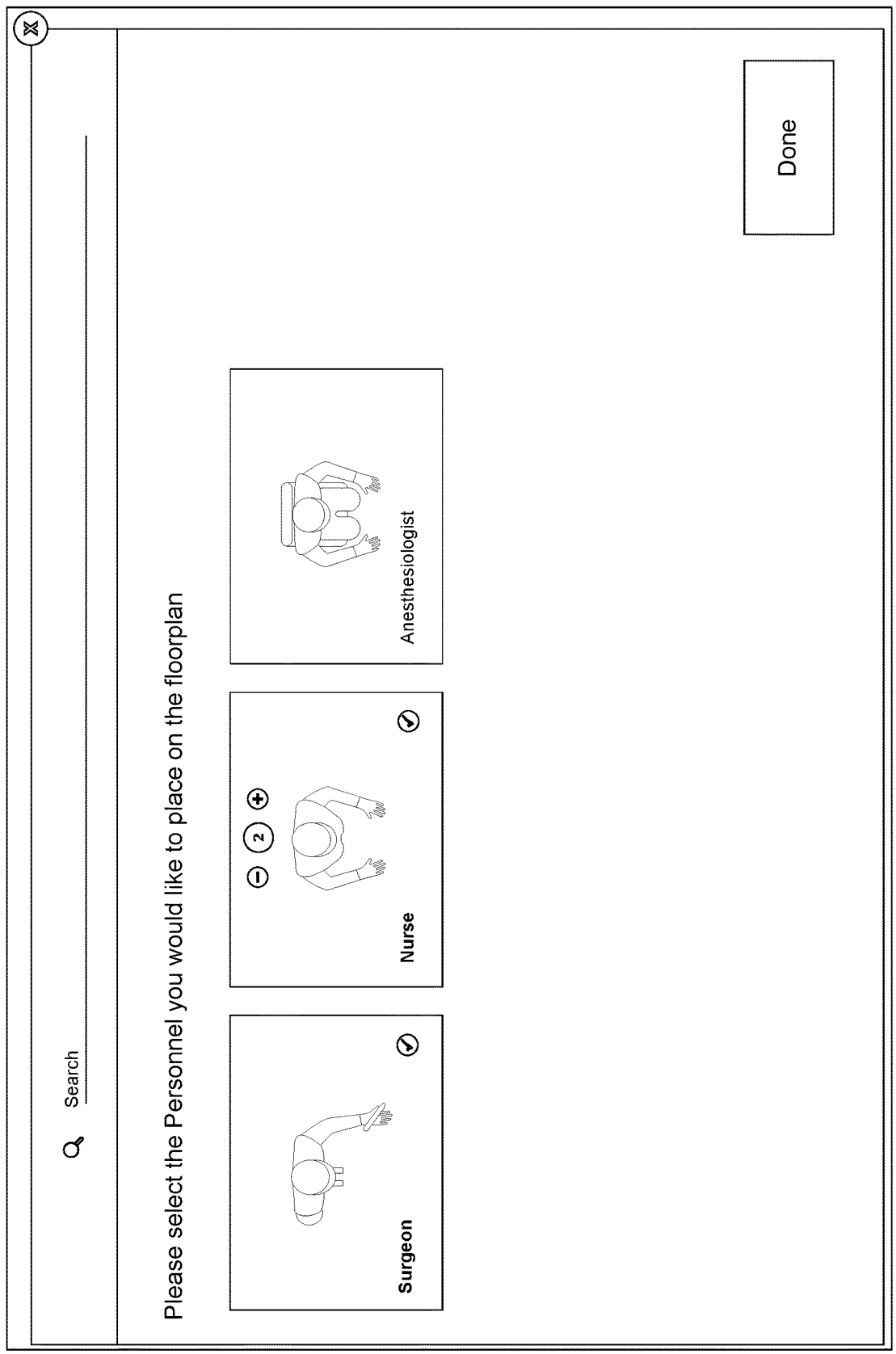
FIG. 10 depicts an interface allowing the user to specify the roles which should be filled by individuals present during the procedure, and the number of people filling those roles.
Figure 11:
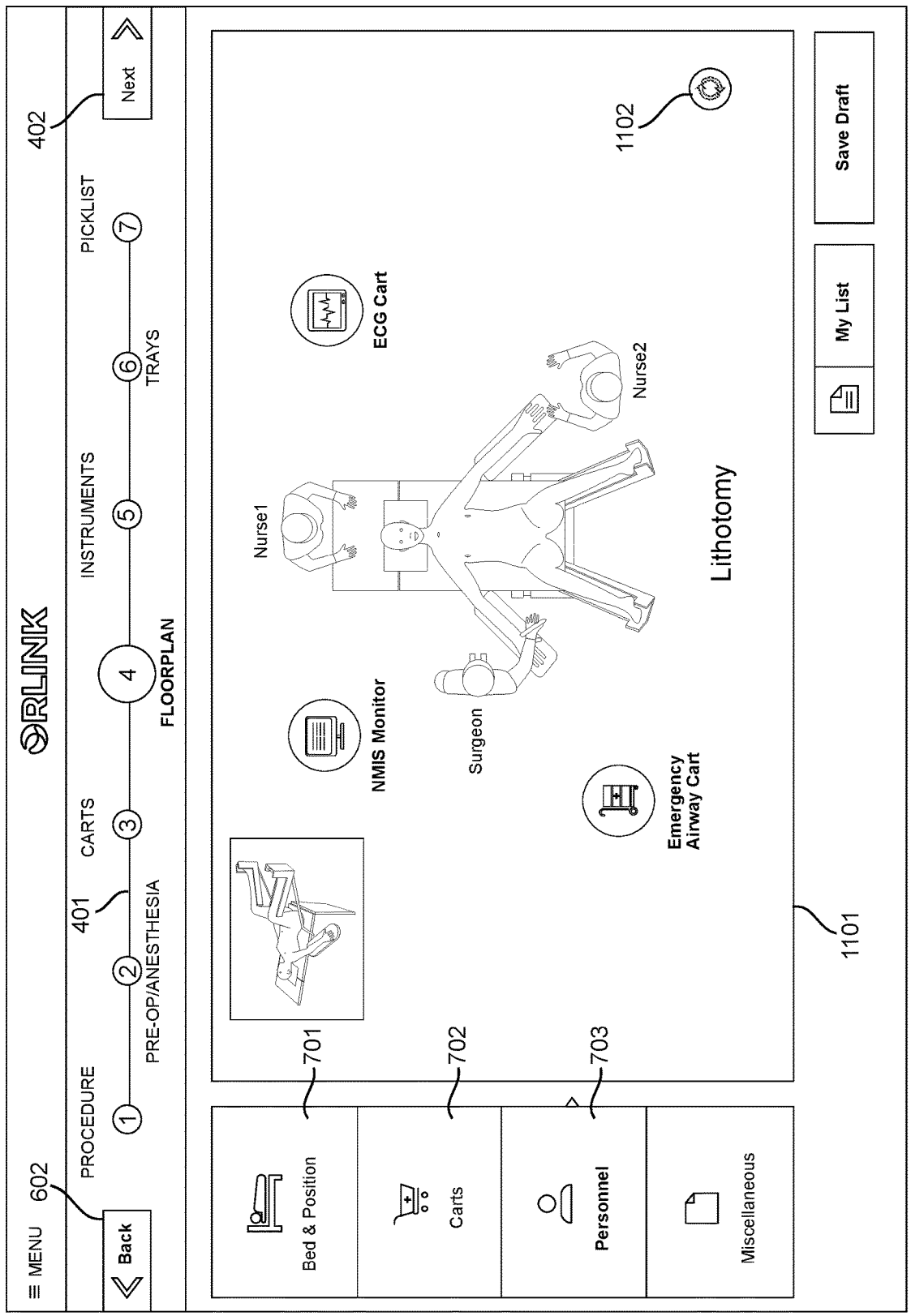
FIG. 11 depicts an interface through which a user would be able to reposition the various people and items shown in the populated floorplan.

FIGS. 7-11 depict interfaces which could be used by a surgeon to specify his or her preferred floorplan setup for a particular procedure. FIG. 7 depicts an interface in which the floorplan is entirely undefined, and presents the user with tools which he or she would use to specify items or personnel that should be present during the procedure. For example, if the user selects the bed and position specification tool 701, he or she could be presented with an interface such as shown in FIG. 8, showing graphical representations of various beds and potential patient positions from which the user could make a selection. Similarly, if the user selects the carts tool 702 he or she could be presented with an interface such as shown in FIG. 9, from which the user could select cart(s) (e.g., carts specified using an interface of the type shown in FIG. 6) which should be present in the operating room during the procedure. If the user selects the personnel tool 703, he or she could be presented with an interface such as shown in FIG. 10, allowing the user to specify the roles which should be filled by individuals present during the procedure, and the number of people filling those roles (e.g., how many nurses should be present). Finally, FIG. 11 shows an image of the floorplan for the operating room with the patient in the position specified by the user, the cart(s) specified by the user, and the personnel specified by the user using interfaces such as shown in FIGS. 8-10. Preferably, using an interface such as shown in FIG. 11, a user would be able to reposition the various people and items shown in the populated floorplan 1101. This could be done using drag and drop functionality of a mouse or touch interface for movement, potentially combined with the use of a rotation tool 1102 for changing orientation (e.g., when the user wanted to change orientation, he or she could select the rotation tool 1102, select the person or item to be rotated, rotate them using a mouse or gestures on a touch interface, and then deselect the rotation tool 1102 when the rotation was complete).

Of course, it should be understood that the description set forth in the context of FIGS. 7-11 of how a user could define his or her preferences for the floorplan of an operating room is intended to be illustrative only, and should not be treated as limiting on how systems or methods implemented using the disclosed technology could implement such floorplan definition functionality. For example, while the interface of FIG. 8 allowed a user to select from a set of static images that would be reproduced on the floorplan, in some embodiments a user could be presented with a set of base images that he or she could then manipulate to obtain an image of a patient and bed configuration which was customized based on that user's preferences for a particular operation. To illustrate, consider FIG. 12, which depicts a base configuration and five potential alternate configurations which some systems implemented using the disclosed technology could allow to be derived from the base configuration through geometric manipulation and built in knowledge of patient physiology and common positioning aids.

Figure 12:
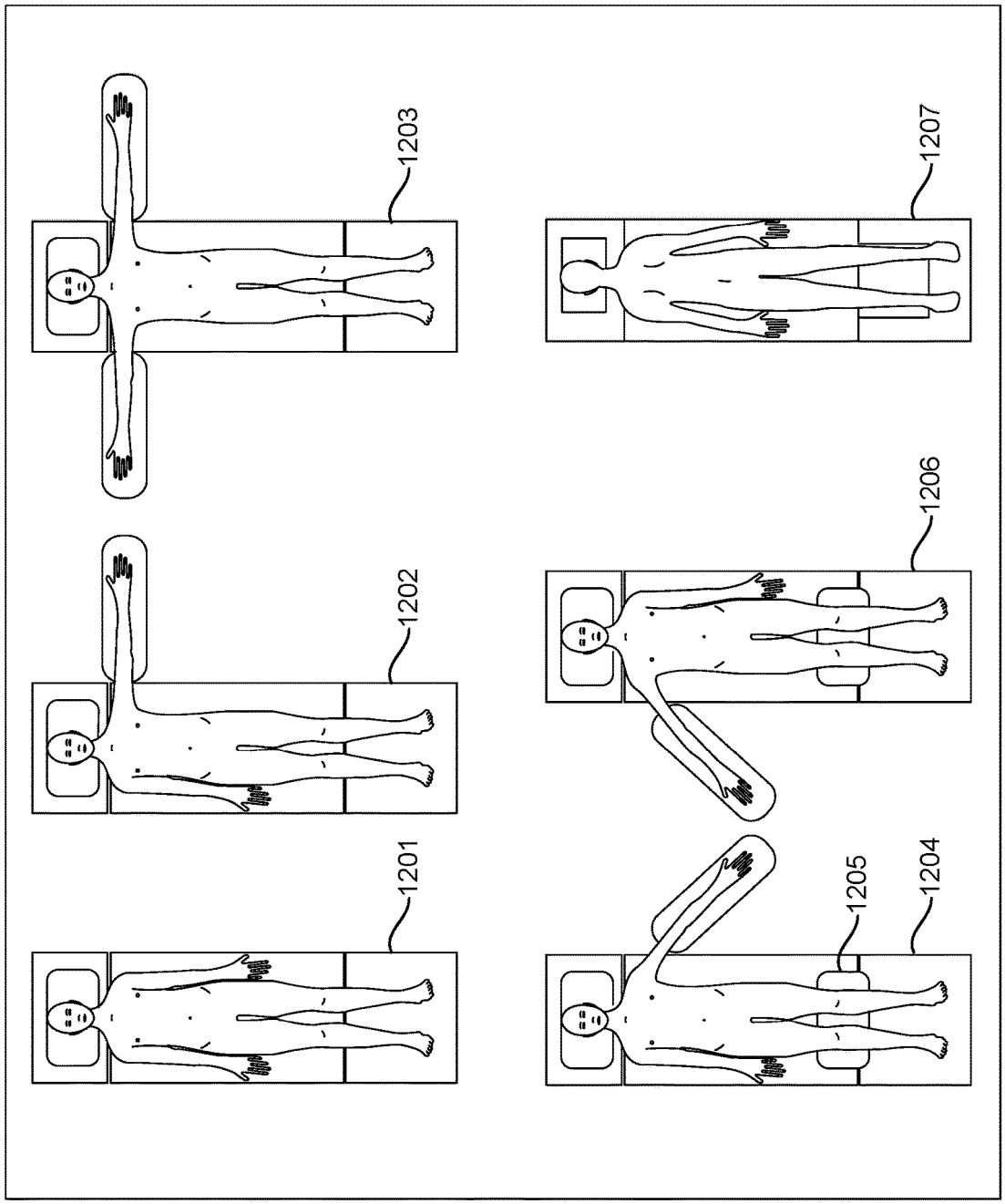
FIG. 12 depicts a base configuration and five potential alternate configurations which some systems implemented using the disclosed technology could allow to be derived from the base configuration through geometric manipulation and built in knowledge of patient physiology and common positioning aids.

In a system supporting this type of position customization functionality, when a user first selects the bed and position specification tool 701, he or she could be presented with an image of a patient in a default position—e.g., the hands tucked supine configuration 1201 shown in FIG. 12. He or she could also be presented with a list of common bed modifications which could be used to specify what, if any, modifications the user desired for a particular procedure. Examples of these modifications could include adding a left arm board or adding left and right arm boards, though other types of bed modifications (e.g., switching from supine to beach chair position, switching to a lithotomy bed, etc.) could also be supported. Preferably, in an implementation which supported bed modifications, when a bed modification was made the patient's body would automatically be moved to reflect the modification. This could be done, for example, by adding anchor points to a virtual representation of a patient and, when a modification was made to a bed, matching those anchor points to corresponding anchor points on a virtual representation of the modified bed. Thus, the disclosed technology could be used to implement a system in which, when a user adds a left arm board, the patient's arm would automatically be shown extended on that arm board based on correspondence between an anchor point in the patient's arm and an anchor point on the arm board (resulting in the supine left arm board 90° configuration 1202), or if the user added both left and right arm boards the patient's arms could both be automatically extended on both of the arm boards if anchor points were included in both of the patient's hands (resulting in the supine arm board 90° configuration 1203).

It should be noted that anchor points such as described in the context of FIG. 12 could be used for more than simply allowing a patient's limbs to automatically reposition themselves when the user makes a modification to the bed. For example, in some embodiments, an anchor point could be movable by the user, thereby providing more precise control than would be possible by simply adding new features to a bed. Thus, in some embodiments, a user could be able to obtain a supine left art board configuration 1204 from a supine left arm board 90° by manipulating the left arm board (e.g., by dragging an anchor point at the end of the arm board farthest from the patient's body) so that the arm board was at the desired angle. The supine left arm board configuration 1204 of FIG. 12 also illustrates another type of modification a user could be allowed to make in some embodiments— adding a cushion, such as the leg cushion 1205 under the patient's knees. Similar types of non-positional manipulations, such as adding sterile towels or heating/cooling pads, or coloring a portion of a patient's skin to indicate the preparation area for an operation may also be possible in some embodiments. Similarly, in some embodiments a user could also be allowed to perform horizontal or vertical reflections of a patient and bed combination (e.g., to obtain the supine right arm configuration 1206 from the supine left arm configuration 1204). Preferably, when a user is able to make this kind of change, the system would automatically replace components of the bed with their mirror images (e.g., left arm board for right arm board) so that the image presented to the user could appear to be simply a reflection of a previous position, even though the data structures used to create that image (e.g., data objects reflecting different arm boards) could be represented differently from each other internally by the underlying system.

While a system implemented to allow a user to manipulate images of patient and bed configurations will preferably automatically modify the position of a patient when a bed is modified, it is also possible that the disclosed technology could be used to implement a system in which a patient and the bed could be manipulated independently of each other. As an example of this, consider the relationship between the hands tucked supine configuration 1201 and the prone arm down configuration 1207 in FIG. 12. In an embodiment which allows switching between these configurations (e.g., by making a selection of a different type of patient position from a dropdown menu which could include items like prone, supine, and lateral) when a switch is made preferably any anchor point associations defined previously would be severed and replaced with anchor point associations reflecting the new orientation of the patient. For example, an association with a left arm board and the patient's left hand could be replaced with an association between the left arm board and the patient's right hand. In this manner, any changes made previously by the user (e.g., adding arm boards, adding cushions, etc.) could be maintained even if the relationship between the patient and the bed was altered.

Of course, it should be understood that other types of variations on the discussion of how a floor plan could be defined are also possible and could be supported in various systems created based on this disclosure. For example, in some embodiments the user could be presented with an interface that allowed him or her to manipulate a floor plan layout in three-dimensional space, such as by incorporating a three-dimensional graphics rendering and physics engine such as the Unity Engine offered by Unity Technologies ApS. It is also possible that, in some embodiments a user would be able to drag and drop various items into a floorplan (e.g., from a sidebar), rather than using a separate selection interface as shown in FIG. 8. Variations on the back end are possible as well. For example, in some embodiments the locations of various items in a floor plan could be stored as raw coordinates, while in others they could be stored as percentages reflecting the relative positions of items in a display, thereby allowing a floorplan to be automatically resized when viewed using different devices having different resolutions. In this type of embodiment, the various images that would be displayed in the floorplan would also preferably be stored in a manner which allows for automatic resizing (e.g., SVG, or other vector based image format), so that viewing interface modifications could be automatically reflected in item size rather than just in item location. Other modifications are also possible and will be immediately apparent to those of ordinary skill in the art in light of this disclosure. Accordingly, the discussion and exemplary interfaces presented in the context of FIGS. 7-12 should be understood as being illustrative only, and should not be treated as limiting on the scope of protection provided by this document for embodiments which include floorplan preference definition functionality.

Figure 13:
FIG. 13 depicts an interface which would allow a user to define his or her preferences with respect to individual instruments.
Figure 14:
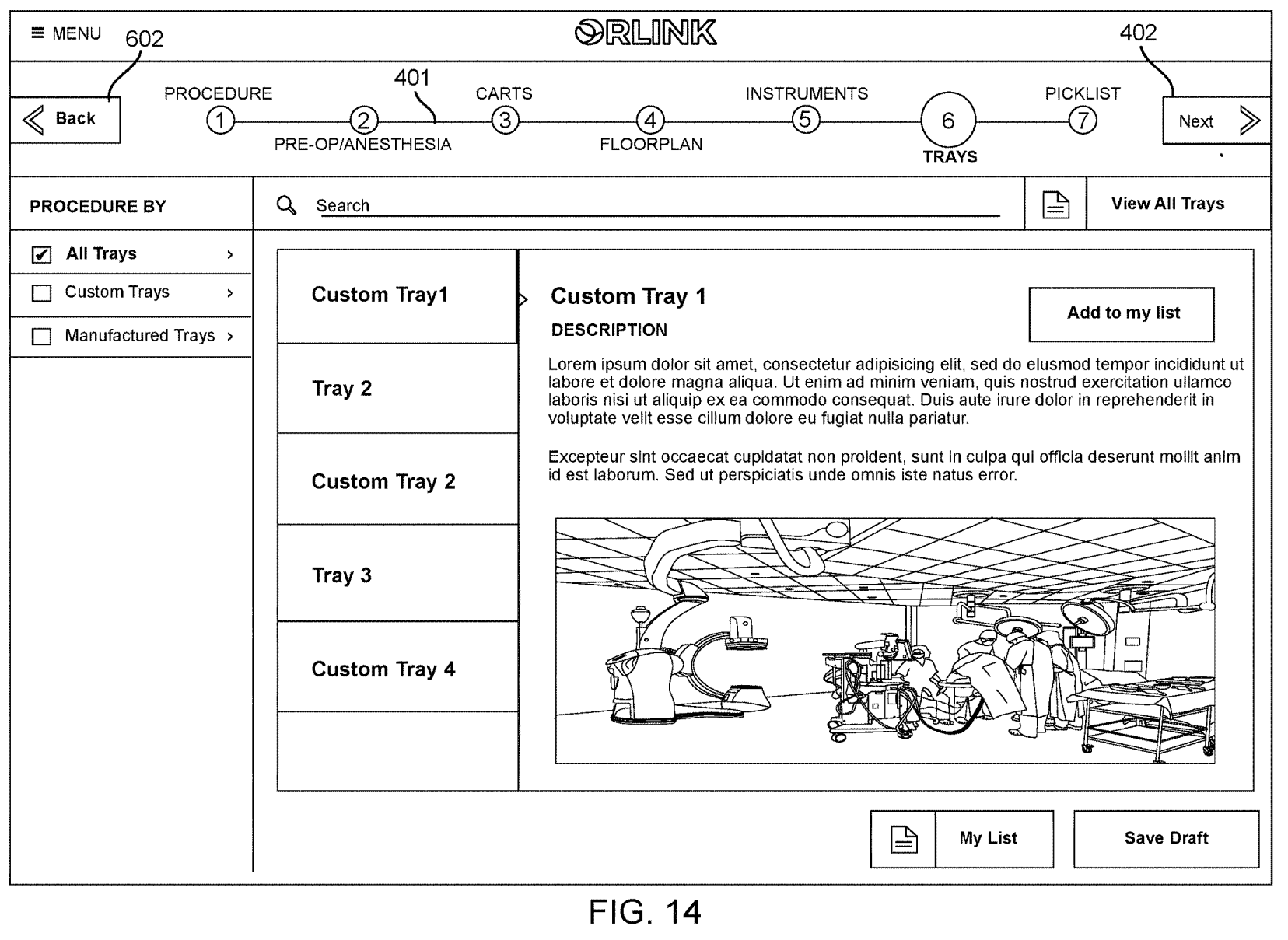
Figure 15:
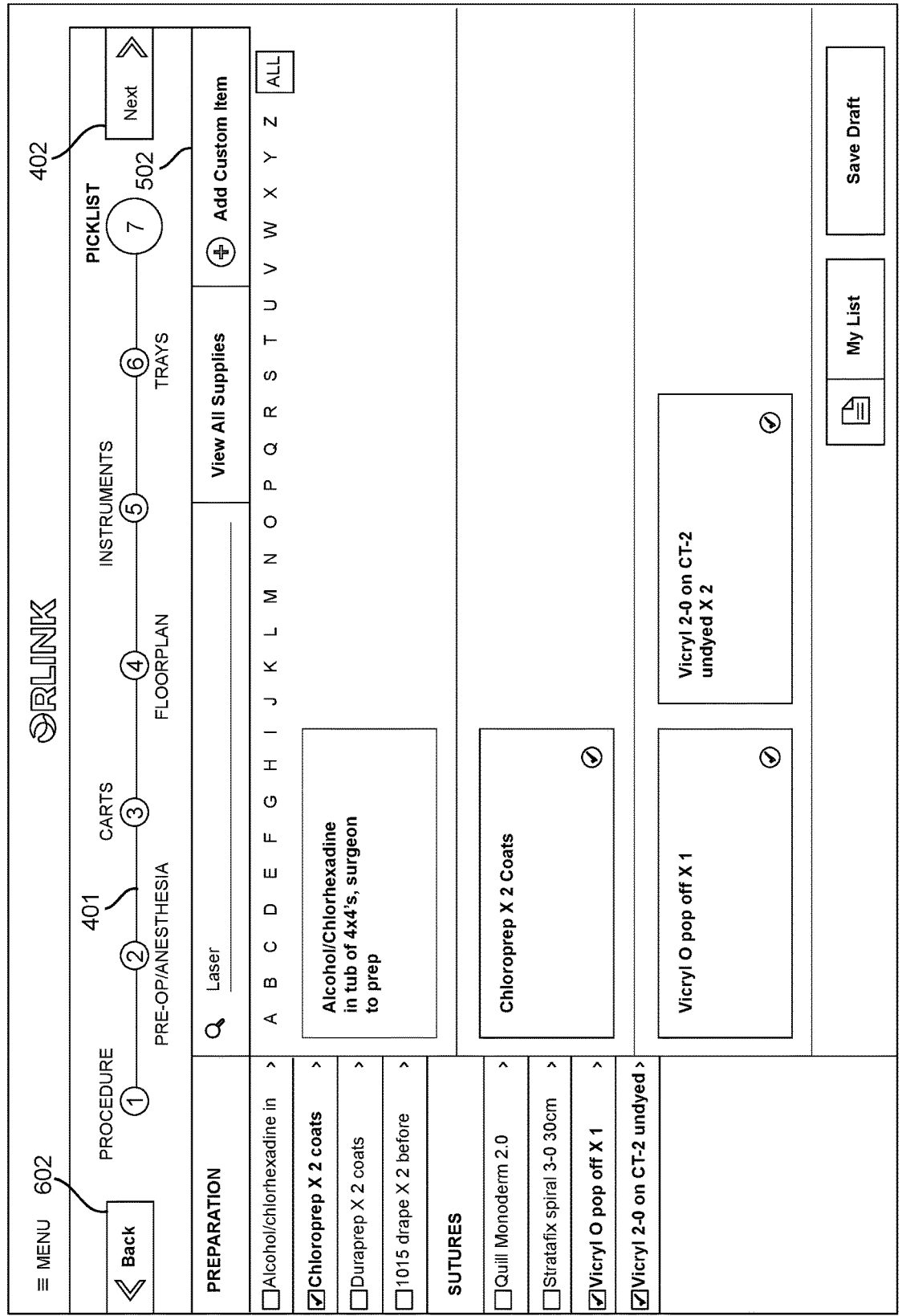
FIG. 15 depicts an interface which would allow a user to define his or her preferences with respect to picklist items.

Moving on from the discussion of floorplan preference definition 206, FIGS. 13, 14 and 15 illustrate interfaces which could, respectively, allow a user to define his or her preferences with respect to individual instruments, trays and picklist items which should be present for an operation. Preferably, these interfaces would be operated in a manner similar to the interfaces of FIGS. 4-6. That is, they would provide lists of items that a user could pick from to indicate their preferences, along with navigation tools for moving from one segment of the preference definition process to another. There could also be custom item creation tools 502 which could provide functionality similar to that described previously with respect to FIG. 5—i.e., allowing the user to define new items that could be presented to him or her as selections going forward, such as by adding textual labels, images, and/or descriptive information for the relevant items. Finally, once the user had filled in all of his or her preferences for a particular operation, he or she could save the preference card and, if he wanted it to be made available to other users, submit it for approval as reflected in steps 211-213 of FIG. 2.

While the above discussion of FIGS. 4-15 illustrated how the disclosed technology could be used to allow a surgeon to define his or her preferences for a particular operation, it should be understood that there are numerous variations on how such preference definition could be implemented, and that the above discussion was intended to be illustrative rather than limiting. For example, it is possible that the disclosed technology could be used to implement a system in which a surgeon could be allowed to customize the sequence for a procedure, either in addition to or as an alternative to one or more of the customization steps described above. To illustrate how this could take place, consider FIG. 16, which depicts an interface that could be presented to display a previously created preference card for the fictitious "Dr. Amily Peterson." In that figure, a set of preference navigation buttons is displayed in the left side of the interface, with the Preop/Anesthesia button 1603 activated. Corresponding to the selection of the Preop/Anesthesia button 1603, a display portion of the interface lists the preferences previously selected for the Preop/Anesthesia phase of the relevant procedure (e.g., no muscle relaxant, head support doughnut, etc.). Preferably, in an interface such as shown in FIG. 16, the user would be able to select other aspects of the previously specified preferences using appropriate preference buttons, and the material presented in the display portion of the interface would change accordingly. For example, if the user wished to see the specified operating room layout, he or she could select the floorplan button 1604 and the system would automatically display the predefined floorplan in the display portion of the interface.

Figure 23:
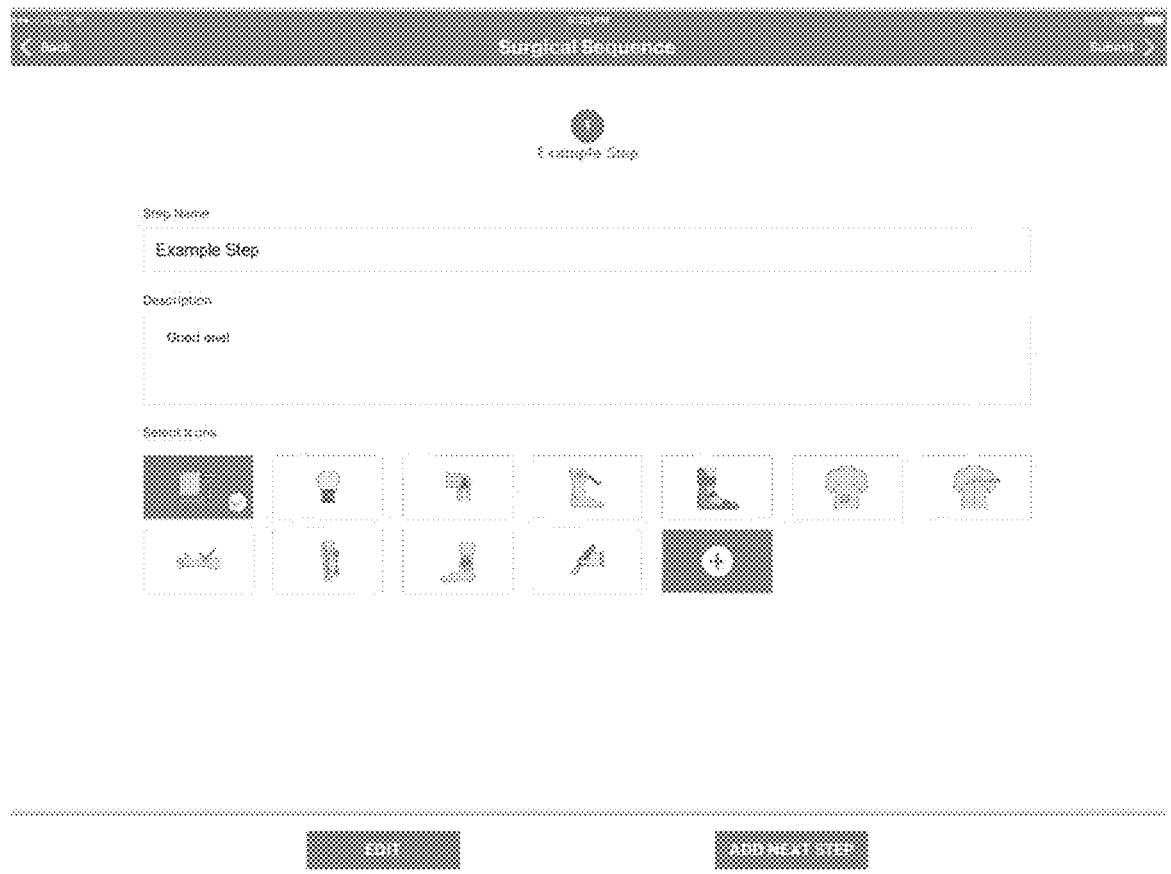
FIG. 23 depicts an interface which could be used to add a step to a surgical sequence.

In that figure, in addition to information showing materials or other items specified for the procedure corresponding to the preference card, there is also a surgical sequence tool 1601 which illustrates the procedure's various phases. As shown in FIG. 16, the sequence display could illustrate default steps which would be expected to be included in the procedure. However, a surgeon could also be presented with a sequence editor 1602 which, when activated, could present an interface such as shown in FIG. 23 which would allow the surgeon to create a custom step such as by defining its name, the icon which should accompany that name, text describing the step and where the step should be included in the surgical sequence tool 1601. Similarly, in some embodiments, a sequence editor 1602 could allow a user to remove steps which had previously added to (or which were included by default in) a surgical sequence display tool 1601. Thus, the disclosed technology could be implemented in a manner which would the user to define an arbitrary number (generally referred to as n) steps which would be included in a surgical sequence display tool 1601.

Other approaches to editing the sequence of a procedure are also possible, and could be supported in various systems implemented using the disclosed technology. For example, some systems implemented based on this disclosure could include functionality to allow existing preference cards to be imported into a sequence for another procedure. To illustrate, consider a total thyroidectomy, a procedure which could be performed to treat thyroid cancer, and which will include neck dissection and laryngoscopy as secondary procedures that could be performed as part of the operation while the patient is still under anesthesia. To reflect this relationship between primary and secondary procedures, in some embodiments when a user activates a sequence editor 1602, he or she could be presented with a list of existing preference cards, and could be allowed to specify that one or more of those cards should be inserted into the card for the total thyroidectomy as part of the sequence for that procedure. In response to this type of selection, the server 101 in the cloud platform 100 could update information for the total thyroidectomy preference card to reflect the incorporation of the other procedure(s). For example, the server 101 could modify the name of a record stored in the database 102 for the "Total Thyroidectomy" preference card to "Total Thyroidectomy with Neck Dissection," "Total Thyroidectomy with Laryngoscopy" or "Total Thyroidectomy with Neck Dissection and Laryngoscopy", depending on which secondary procedure(s) had been incorporated. In this way, when a surgeon (or other medical personnel) later saw that preference card listed, they would immediately know that that preference card was a compound preference card, as well as what procedures the compound preference card included.

Additionally, it is possible that some embodiments might not only support functionality for allowing preference cards to be combined, but might also include semantic processing which recognizes the implications of combining preference cards and responds appropriately. To illustrate, consider the case of a compound preference card for a primary procedure (e.g., a total thyroidectomy) and one or more secondary procedures (e.g., neck dissection, laryngoscopy). In some embodiments which allow for such compound preference cards, when a compound preference card is created a check could be run to determine overlap between items which are needed in the primary and secondary procedures, and the user could be presented with a control panel which indicates and allows him or her to change the number of duplicate items, thereby reducing waste associated with the procedure. In this way, the creation of compound preference cards could not only make it easier for a physician to define his or her preferences for a particular procedure, but could also improve performance of the procedure relative to what would have been expected if each of the individual preference cards were considered in isolation.

Variations on aspects of preference definition are also possible beyond the addition of sequencing functionality. For example, while the discussion of FIGS. 3-16 focused on defining preferences for particular medical procedures, in some embodiments, it is possible that preferences may be defined in manners other than on a per procedure basis. To illustrate, consider FIGS. 18A and 18B, in which those two figures, when placed vertically adjacent to each other with FIG. 18A above FIG. 18B, depict an interface which could be used to define preferences for a surgeon which are not specific to any particular medical procedure. As another variation, while the discussion of FIGS. 3-16 focused on preference cards which were specific to particular hospitals, in some embodiments it may be possible for a physician to create a preference card which was not associated with a hospital and then use that preference card for the procedure it covered whenever he or she went to a new hospital, as opposed to creating a new preference card for each institution. As yet another example of a potential variation, while the above disclosure focuses on preference cards which were specific to particular physicians, it is possible that the disclosed technology could be implemented to support template preference cards which are not specific to any physician. For instance, in some embodiments, the server 101 and database 102 in a cloud based platform 100 could be configured to maintain a library of pre-defined preference cards (e.g., preference cards created using interfaces such as shown in FIGS. 3-16 which are anonymized of physician and hospital information) which could include various default information likely to be relevant to a particular type of operation regardless of the physician performing it. In such an embodiment, when a physician wished to define his or her preferences for a particular operation, he or she could retrieve and build on the pre-defined template for that operation, rather than having to create a new preference card from scratch.

It should be understood that, while the discussion of FIGS. 3-16 focused on the creation and/or editing of a preference card by a surgeon, the disclosed technology may be implemented to support and/or manage more complicated editing procedures as well. For example, in practice, it may be that most edits to a preference card would be made, not by a surgeon, but by an OR nurse implementing the surgeon's instructions. For instance, if a surgeon discovers during a procedure that a particular item is unnecessary, he or she could ask an OR nurse to remove it from his or her preference card for that procedure, and the OR nurse could make the change after the operation was complete. As another example, it is possible that different types of users might create different types of preference cards, or be responsible for defining different aspects of a single preference card. For instance, in some embodiments, rather than having pre-op anesthesia be a phase in a preference card which would be created/edited by a surgeon, there might be a separate anesthesia preference card which would be managed by an anesthesiologist, or an anesthesiologist might be responsible for filling in anesthesia information on a preference card which is otherwise completed by a surgeon. Other similar types of variations are also possible, and will be immediately apparent to those of ordinary skill in the art based on those illustrative examples.

Just as some embodiments may allow more complicated preference editing and/or creation workflows, embodiments may also include additional functionality to help manage those workflows within the context of the institutions where they would take place. For example, to ensure that preference cards are not changed inappropriately, a system implemented based on this disclosure could apply rules after a change is made which would cause the change to be routed to one or more designated individuals (or individuals with designated roles) for approval. For instance, if a change is made by an OR nurse, then a rule could be triggered which would send that change both to a hospital administrator and the surgeon whose preference card was changed and which would require approval from both of those individuals before the modified preference card could be published and made available to other users in the hospital. Similarly, in addition to (or as an alternative to) considering user roles, in some embodiments rules could trigger different approval workflows based on type of change made. For instance, in some embodiments, there could be a rule that whenever a user makes a change by adding or deleting an item in the "Carts" category, that change would have to be routed to and approved by a hospital administrator even if the user was a surgeon modifying his or her own preference card.

As will be appreciated by those of ordinary skill in the art, there is a broad variety of potential rules and approval workflows which could be implemented. Accordingly, in some implementations, when a hospital is initially given the ability to allow its users to access a system using the technology, that hospital's approval conditions and workflows may be defined by a set of default rules. The hospital administrator may then be given the ability to define new rules and workflows which he or she believed would be more appropriate, and those rules would be applied to preference cards used at that administrator's institution. In this way, a system implemented using the disclosed technology could provide for both ease of deployment and customization by individual institutions without compromising the control provided to users regarding what preference cards would and would not include.

Figure 17:
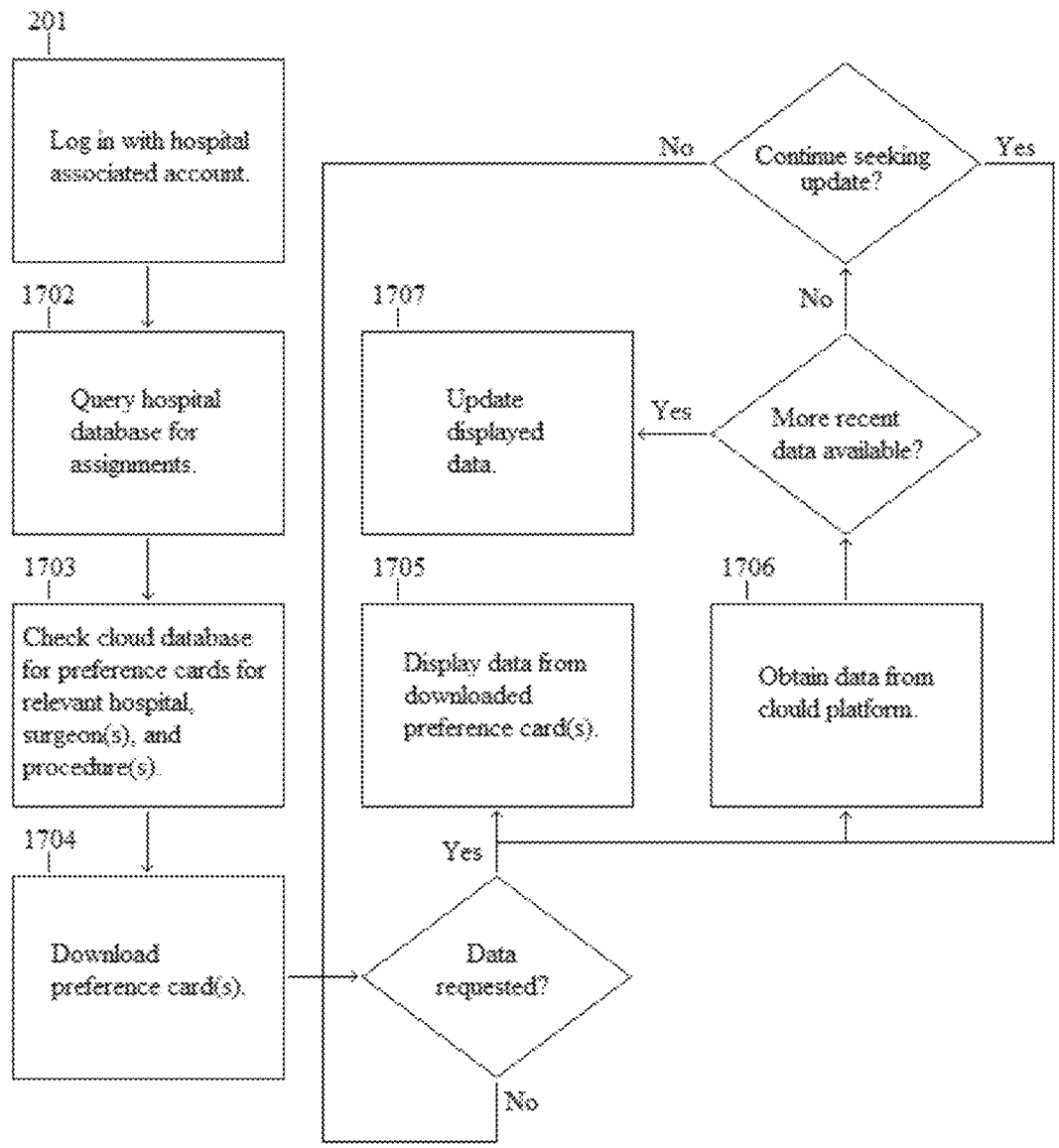
FIG. 17 depicts a process which could be supported in some systems implemented based on this disclosure is to allow medical personnel to have access to time critical information even when they are in a location (such as many operating rooms) with little or no network connectivity.

Turning now to how a preference card could be used once it is created, as shown in FIG. 17, one potential use which could be supported in some systems implemented based on this disclosure is to allow medical personnel to have access to time critical information even when they are in a location (such as many operating rooms) with little or no network connectivity. Initially, in the process of FIG. 17, an OR nurse or other individual responsible for setting up an operating room according to a surgeon's preferences would log in 201 with an account associated with the hospital where a procedure would take place. At this point, the server 101 on the cloud based platform 100 could recognize the user's role and hospital association and query 1702 the database for the associated hospital to find the user's work assignment for that day, and what surgeon(s) would be performing the procedures that the user would be responsible for. The server 101 could then check 1703 in the database 102 on the cloud based platform for the preference card(s) for the relevant procedure(s) which had been saved by the surgeon while logged into an account for the relevant hospital. These preference cards could then be downloaded 1704 to the user's mobile device, essentially forming a local storage of data related to the particular user's preferences, including information retrieved from a particular hospital's EHR system such as inventory, team member contact information and other data used by a mobile user to create preference cards and procedures and to communicate to the platform and other system actors. This information preferably also resides in the database 102 of the cloud based platform 100 and is synchronized whenever the mobile device such as a tablet connects to WiFi. While the master data initially resides in the cloud and on hospital EHR's, certain sub sets of data resides on the mobile user devices so it can be obtained even when no network connection was available.

Subsequently, as the user requested data from a preference card, an application on his or her mobile device could provide 1705 that data from the downloaded information, either immediately, or after a check had been performed to determine if it was possible to obtain the data from the cloud platform. If the data was provided 1705 immediately, then, in parallel, the application could attempt to obtain 1706 that same data from the cloud platform 100 and, if more recent data was available (i.e., a connection to the cloud platform was available and a more recent version of the data from the downloaded preference card(s) was available from the cloud platform), could update 1707 the information provided by the mobile device with the more recent data from the cloud platform. If more recent data was not available, a check could be run to determine if a more recent version of the requested data would still be helpful (e.g., because no new data had been requested) and, if it would, the process of trying to obtain and provide new data could be repeated. Otherwise, the system could simply wait until the next time data was requested, and repeat the displaying 1705, obtaining 1706 and updating 1707 steps described above when it was.

Of course, it should be understood that, while FIG. 17 and the associated discussion focused on retrieval of preference card information, similar techniques could also be used for other potentially time sensitive information which might be needed during a procedure performed in an area with little or no network connectivity. For example, in some embodiments, a remote cloud platform could identify best practices information for the procedures that the user would be responsible for, and download that information to the mobile device so that it could be made available independent of the (un)availability of network connectivity. Similarly, in an embodiment which maintained information regarding what types of additional supplies were likely to be needed during a particular operation, the cloud based platform 100 could retrieve information from the database of the hospital where the procedure(s) would take place regarding which of those additional supplies were in stock and where they were located, and then download that information to the mobile device so that it could be made easily available as needed during an operation. Accordingly, the discussion above of ensuring the availability of preference card information should be understood as being illustrative only, and should not be treated as limiting.

Just as the disclosed technology could be used to make preference card information available during a procedure, it could also be used to capture information regarding a procedure and, if appropriate, propagate that information back to a preference card and/or electronic health care records for an individual patient, or otherwise communicate it to the appropriate person/entity. As an example of this, consider the case of determining what materials/supplies were not used during a procedure and whether such materials/supplies should be removed from a preference card in the future. To support this type of functionality, in some embodiments, after a procedure has been completed, an inventory could be taken of unused items (e.g., by scanning those items with a bar code or QR code scanner, or by manually identifying them) and information indicating what items were not used could be sent to the cloud based platform 100 (e.g., as part of a notes field in the preference card for the procedure). Subsequently, a notification could be sent to the surgeon who performed the operation informing him or her of the excess, and suggesting that he or she might wish to edit his or her preference card to remove the unused item(s), thereby avoiding waste and reducing the cost of the procedure for the patient.

As another example of how the disclosed technology could be used to capture, and appropriately propagate/apply information regarding a procedure, consider the potential for the disclosed technology to be used for capturing notes or other information during a procedure. This could be done, for example, by incorporating speech recognition functionality into software which makes preference card information available in an operating room (e.g., a mobile application such as could perform steps of the type shown in FIG. 17), and then using the speech recognition functionality to record statements regarding a particular operation as it was taking place. For example, this type of speech recognition software could be incorporated into a type of surgical digital assistant which, by analogy to digital assistants like Siri (provided by Apple) or Cortana (provided by Microsoft) could have always on listening functionality which would be triggered by certain key words or phrases (e.g., "Surgica, take a note"). Such a note could then be stored temporarily by the software running the surgical digital assistant, and after the procedure could be propagated back to the EHR for the patient on whom the procedure was performed (if the note related to a specific patient) and/or to the cloud based platform 100 so that it could be incorporated into the database 102 for subsequent analysis (if the note wasn't patient-specific).

Of course, it should be understood that, in some embodiments which include a surgical digital assistant such as described above, such a surgical digital assistant could do more than capture spoken words. For example, in some embodiments where a surgical digital assistant is provided, such an assistant could detect emotional information such as stress levels reflected in the speech of the physician or other participants. In this type of embodiment, in addition to including speech recognition technology, a surgical digital assistant could also include voice recognition technology to identify the speaker for a particular statement, and stress level identification technology for identifying whether (and how much) stress the speaker was under when he or she made the statement. Then, when a statement was made which indicated that the speaker was under stress, the surgical digital assistant could record the time, content, speaker and stress level of the statement in a notes field of a preference card, and this information could later be uploaded to the cloud based platform 100 for review and analysis once the procedure was complete and network connectivity became available (if it hadn't been available during the procedure itself).

Surgical digital assistants could, in some embodiments, be used to provide information rather than only to capture it. For instance, in some embodiments, a surgical digital assistant could be configured to recognize statements from operating room personnel like "Surgica, show me a XYZ retractor" and the surgical digital assistant would display an image of the desired retractor retrieved from the cloud based platform (if a connection to the cloud based platform was available) or from a local store downloaded in a manner such as described previously in the context of FIG. 17. As another example, in some embodiments, a surgical digital assistant could make use of the context in which a statement is made to allow it to provide meaningful responses to more ambiguous queries. To illustrate, consider a statement made in an operating room like "Show me carts for this room." In some embodiments, a surgical digital assistant could be configured to respond to such a statement by determining the room being referred to (e.g., by comparing an internal clock with schedule data for the user of the mobile device hosting the digital assistant to determine which room that individual was expected to be in at the time the statement was made), determining a procedure for the room (e.g., by comparing room schedule data against an internal clock), retrieving preference card information for that procedure (e.g., from local memory), and presenting pictures of the carts specified in that preference card. Similarly, in some embodiments, the context in which information is provided could also be used to help provide meaningful answers to ambiguous requests. For instance, in some embodiments a surgical digital assistant could be configured to respond to a statement like "show me the critical instruments for this case" by first determining the preference card for the case (e.g., using comparisons of scheduling data and an internal clock as described previously) and then identifying items which had been specified using an instruments interface (e.g., as shown in FIG. 13) as the critical instruments (as opposed to items which might have been included in a tray specification interface but which were not identified in the instruments interface).

It is also possible that a surgical digital assistant could make use of contextual knowledge to provide an even richer picture of events during a procedure. For instance, in some embodiments, a surgical digital assistant could be configured to recognize potentially relevant sounds other than a human voice (e.g., glass breaking, sounds made by surgical tools, saws, drills, etc.). In such an embodiment, information about whether (and when) these sounds were captured could be recorded in the same manner as notes, thereby providing a record of events during a procedure even when no explicit notes are made. These sounds could also be matched against expected sequences or timelines for a procedure to confirm that the procedure was progressing as expected and to allow detected events (e.g., if a surgeon says a note should be taken) to be placed in the context of what is happening during an operation, either in addition to or as an alternative to being contextualized through use of time.

While the information capturing functionality described above would be beneficial, it should be understood that a surgical digital assistant as described could provide benefits beyond simply facilitating the capture of information. For example, just as a general purpose digital assistant such as Amazon's Alexa can be configured to integrate with and execute functions through third party applications, a surgical digital assistant can be configured to integrate with third party applications and perform actions which could be beneficial during an operation. To illustrate, consider a case where a physician wishes to consult with one of his or her colleagues during an operation. With a system which is implemented using the disclosed technology and which includes a digital surgical assistant, this could be done by speaking a predetermined phrase such as "Surgica, please locate Dr. Smith and patch him into OR via voice or FaceTime." In response to such a command, software running on the mobile device which provides the surgical digital assistant functionality could check its local contacts for a doctor matching the name "Dr. Smith" and, if network connectivity was available, attempt to contact him or her via voice or video while making a confirmation statement such as "Calling Dr. Smith Now." Alternatively, if there was a problem with execution of the command (e.g., there were multiple physicians matching the name "Dr. Smith," or no physicians matching the name "Dr. Smith," or if no network connectivity to support a voice or video connection was available), the surgical digital assistant could inform the physician of the issue and request additional information if and as appropriate (e.g., if there was network connectivity available but it was unclear who "Dr. Smith" referred to, the surgical digital assistant could ask the physician for information to use in disambiguating the reference to "Dr. Smith").

Just as a surgical digital assistant could be configured to do more than facilitate the capture of information, the disclosed technology could also be used to implement a system in which a surgical digital assistant did more than respond to commands during a procedure. For example, it is possible that, based on information such as the nature of a procedure being performed (which could be determined based on a preference card previously downloaded from the cloud based platform 100), how much time had elapsed since that procedure began, and/or sounds detected during the procedure, a surgical digital assistant could be configured to make proactive suggestions based on requirements information maintained by the cloud based platform and downloaded to the mobile device for accessibility during the procedure. For instance, in response to detection of a request for a heart valve, the surgical digital assistant could check for what other equipment would be necessary for the heart valve to be used, then, if that equipment was not already present, could ask if that should be requested as well. for example, if the surgeon stated "please retrieve a heart valve from storage" the surgical digital assistant could check if there were calipers available to make a measurement for the heart valve size and, if there were not, could determine the name of the surgeon who had just spoken from its stored preference card information and make a follow up statement like "Dr. Jones, should I also initiate retrieval of calipers?" Then, after receiving an affirmative response from the relevant physician (e.g., "Confirmed, Surgica"), the surgical digital assistant could automatically initiate a command to retrieve the calipers from its location in the hospital's inventory (e.g., by displaying a message on a display in the operating room saying where the calipers could be located in the hospital's stores).

This same type of approach could also be used by a surgical digital assistant to make suggestions based on best practices information rather than simply based on requirements as described above. For example, a surgical digital assistant could be configured to monitor time elapsed from the beginning of a procedure and, if more than three hours elapse from the beginning of the procedure, provide a proactive reminder to the OR staff regarding the importance of draining urine using a foley catheter. Such a proactive reminder could be in the form of an audio prompt, a written reminder on a display located in the OR, or some other appropriate form given the context and the nature of the equipment available in the particular embodiment. Similarly, a surgical digital assistant implemented based on this disclosure could be configured to listen for sounds indicating application of a tourniquet (e.g., a request by a surgeon for a tourniquet), and use such sounds as a trigger to start a two hour timer, after which the surgical digital assistant could provide a prompt suggesting that the tourniquet be deflated.

Of course, it should be understood that, in cases where it is maintained, best practices information could be used for more than simply providing reminders during an operation. To illustrate, consider an embodiment in which preference information could be used as a knowledge base to assist physicians when they are defining their own preferences for particular procedures. In such an embodiment, if a physician was creating a preference card for a particular procedure, and the previously created preference cards at the cloud based platform indicated that a certain type of disposable was selected with some threshold frequency (e.g., 80% frequency over 1,000 existing preference cards), then that disposable could be auto-suggested by the system for inclusion in the preference card being created (e.g., by highlighting the selection for that disposable in an interface such as shown in FIG. 15, by presenting a pop-up to the user, or through some other technique as might be appropriate given the context of a particular embodiment).

These types of suggestions could also be triggered by circumstances other than commonality of preferences. For example, in some embodiments, data regarding the performance or outcome of a procedure could be anonymized and propagated back to a cloud based platform for analysis using machine learning algorithms to identify potential practices which could be used to improve patient outcomes, reduce waste, or achieve other useful objectives. For instance, in some embodiments of this type, the time elapsed during a procedure could be captured and sent back to the cloud based platform, and this information, combined with the preference cards for the relevant procedures could be subjected to machine learning algorithms (e.g., a machine learning algorithm based on Bayesian inference) to identify insights such as if inclusion of (or omission of) various disposables, carts, etc. was associated with increased (or decreased) time for completing a procedure. Similar analysis could be performed to identify if certain choices which could be made prior to a procedure were associated with increased or decreased likelihood of stressful events (as could be detected using a voice enabled surgical digital assistant), waste (as could be identified by inventorying unused equipment at the end of a procedure) or other items of interest (e.g., adverse patient outcomes). Then, using these automatically generated best practices as a foundation, a system implemented based on this disclosure could make suggestions (e.g., by notifying a physician when he or she was creating a preference card, or by notifying an administrator who might be setting policies for a hospital) which could reduce cost and risk and improve patient outcomes for procedures facilitated by the system.

In some embodiments, suggestions based on automatically derived best practices could also (or alternatively) be made during a procedure rather than during the creation of a preference card. For example, in some embodiments, it is possible that information gathered using the disclosed technology (e.g., information about sounds captured during various procedures, preference card information, etc.) could be provided as input to train multiple machine learning algorithms to answer questions such as "should a specialist be asked to consult on this procedure" or other questions which could have an impact on a patient outcome or other objective. Then, during a procedure for which the machine learning algorithms had been trained, the contextual information gathered the procedure could continually be fed to the machine learning algorithms and, if they both provided the same answer to one of the questions that answer could be provided to the operating room personnel as a proactive suggestion. To illustrate, consider an embodiment which was designed to provide proactive recommendations on whether a specialist should be consulted. In such an embodiment, two machine learning algorithms, e.g., the Multi-Perspective Context Matching model proposed by Wang et al. in *Multi-Perspective Context Matching for Machine Comprehension* (arXiv:1612.04211), and the Bi-Directional Attention Flow network proposed by Deo et al. in *Bidirectional Attention Flow for Machine Comprehension* (arXiv: 1611.01603), could be independently trained to answer the question "should a specialist be consulted now?" Then, during an operation, if both of those models provided the answer "yes" to that question, an alert could be provided such as "Dr. Jones [assuming that the doctor performing the procedure had the surname of Jones], you may want to consult a specialist regarding this procedure, when possible." Thus, the above disclosure of using automatically determined best practices in the context of preference card creation should be understood as being illustrative only, and should not be treated as limiting.

It should be understood that making suggestions based on automatically derived best practices information is not the only way that the disclosed technology could potentially reduce risk and/or improve patient outcomes. As another example of how this could take place, consider how an operating room floorplan (e.g., as could be defined using an interface such as shown in FIGS. 7-11) could be used to ensure proper patient positioning. To facilitate this, in some embodiments, surgical team members may be able to visually align the patient with a two-dimensional (2D) or three-dimensional (3D) preset image to ensure the patient is in the proper location on the operating table in the operating room. Such a technique can be practiced using positioning sensors that determine the patient's physical orientation by measuring the location of the patient and other items within the operating room (e.g., carts, workstations, operating table).

Alternatively, if such sensors are not available, position can be measured by a member of the surgical team recording the patient's position on an interface provided by a mobile application in the operating room. When the patient is correctly positioned within the operating room in accordance with a preference diagram uploaded to the cloud-based platform (or downloaded to a computing device in the operating room, in a situation where network connectivity to the cloud based platform was unavailable), an indicator could be displayed by a computing device associated with a surgeon or a member of the surgical team. For example, the indicator could be presented by an application executed by the computing device to provide visual confirmation that the patient has been aligned correctly.

It should be noted that this type of positioning functionality could be supported for both 2D and 3D positioning, as 2D imaging may be inadequate for certain surgeries which need ultra-precise alignment in 3D space. In such a case, positioning may require the patient to be scanned, for example with an in-room computerized tomography (CT) scanner or a cone-beam CT scanner in order to verify the patient's position within the operating room. To accommodate this, various embodiments of the disclosed technology may utilize photo sensors that capture images from multiple angles and enable visual comparison (e.g., via augmented reality) for position confirmation.

It should also be noted that, in some embodiments, the same or similar interfaces can be used to ensure that other individuals (e.g., nurses) and items (e.g., carts, tools, workstations) are located in the position preferred by the surgeon. Moreover, an interface displayed on a mobile device may include a list of the carts, materials, tools, disposables, and other items needed to prepare for and perform a surgical operation. Such an interface enables the surgeon or another member of the surgical team to confirm the item(s) are present prior to beginning the surgery and to ensure that the surgeon's preferences are adhered to.

Figure 19:
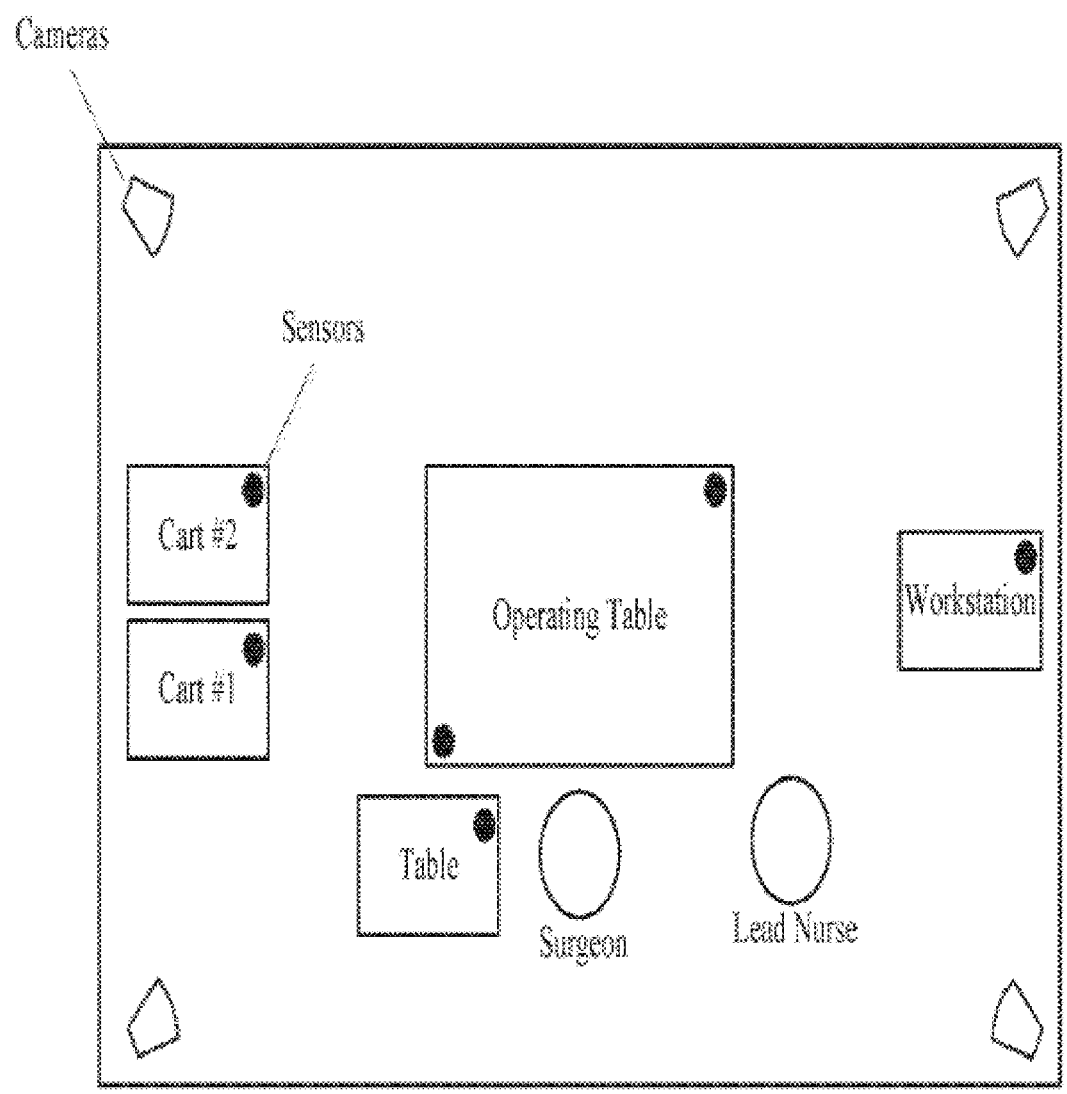
FIG. 19 depicts an operating room that has been arranged in accordance with a surgeon's preferences.

To illustrate how this type of positioning may be facilitated using the disclosed technology, consider FIG. 19, which depicts an operating room that has been arranged in accordance with a surgeon's preferences. As shown here, a system such as could be implemented based on this disclosure can include visual sensors (or some other type of sensors) to aid in the physical and anatomical positioning of individuals (e.g., patients and surgical team members) and items (e.g., carts, tools, operating table) within an operating room. Cameras and various sensors (e.g., capacitive sensors, resistive sensors, rubber stretch sensors, textile sensors, haptic sensors, piezoelectric sensors) can be used to measure different physical properties and dimensions. Here, for example, a patient may be precisely aligned on an operating table when the system detects the operating table's sensors and compares them to one or more markers (e.g., temporary tattoos or other surrogate reference points) of the patient.

In some embodiments, the measurements produced by sensors such as shown in FIG. 19 may be processed in real time by a computing device (e.g., by the cloud-based platform or a user device associated with a surgical team member) to accurately determine the precise positioning of a patient. Thus, sensors may be used to provide a quantitative measure for specifying compliance with a surgeon's preferences. Moreover, the sensors can be placed within the operating room near the patient in any pattern (e.g., a linear array, rectangular grid, circular or irregular arrangement). As noted above, the surgeon or some other member of the surgical team can use a computing device (e.g., a mobile phone, tablet, or personal computer) to monitor compliance with the surgeon's preferences (which may be specified using a digital preference card). The measurements may work in tandem with information stored locally on a computing device (e.g., of a surgical team member) when the computing device is not connected to a network and/or with information stored remotely on the cloud-based platform when connected to a network. As described previously, in some embodiments, specified alignment images may be locally stored on the computing device and later synced with the cloud-based platform for subsequent retrieval by another computing device. In some embodiments, all of the items within the operating room (e.g., cards, tables, workstations) may be motorized objects that are able to automatically or semi-automatically self-locate and self-position themselves within the operating room in accordance with the surgeon's preferences using beacons and/or sensors. In such embodiments, the operating room may be able to assemble itself and become fully or semi-automated.

In some embodiments, one or more beacons may be placed along each entranceway of the operating room to monitor the individuals and/or items that enter and leave the operating room. For example, a positioning beacon could track the WiFi signal emitted by an individual's computing device (e.g., a surgical team member's mobile phone) to determine the ingress time, egress time, and total time spent in the operating room. Similar techniques could be used to monitor the movement of physical therapists, nurses, technicians, etc., in order to better track costs and operating room time. Beacons may also be used for guidance, for example, into a central supply room for disposable supplies required during a surgery. In some embodiments, augmented reality techniques may be used to recognize important elements (e.g., bar codes, QR codes, or identifiable product numbers or features) within a hospital inventory. For example, augmented reality techniques may be used to recognize surgical instruments, disposable supplies, etc. By using comparative recognition and analysis, the necessary item(s) can be readily located within the hospital inventory (e.g., a supply room). Similarly, items that are unused during a surgical operation could be scanned (e.g., using a camera of a mobile computing device), recognized as a match with a database entry, and removed from a standard pick list associated with a specific surgical procedure completed by a particular surgeon. Such a technique can limit the waste caused by unused surgical equipment and thereby save surgical costs.

Other computing devices may also function as a beacon for tracking the location of certain individuals or items within an operating room (or some other environment). For example, beacon sensors may also be able to detect signals wirelessly broadcast by a mobile phone and, thus, recognize the mobile phone as an "identification badge" for a corresponding individual (e.g., a member of the surgical team). Other computing devices (e.g., tablets, personal computers, and wearable devices, such as Apple watches, Fitbits, etc.) can also be recognized by the beacon sensors. Detection enables the cloud-based platform to calculate the number of times an individual enters/exits the operating room (e.g., for supplies), the location of the individual during certain segments of the surgery, etc. These criteria can be studied to improve the efficiency of the surgical team and the operating room/hospital as a whole.

Object and facial recognition technology can also be used to provide functionality similar to that described above for beacons and augmented reality. For example, in some embodiments, an operating room might be implemented with an overhead camera having either built in or remote object and/or image recognition technology, and such a camera could be used to track the movements of people and objects in the operating room. For example, in some embodiments, a camera with built in or remote artificial intelligence capacity could be trained to recognize objects which are at risk of being left inside a patient after a procedure (e.g., clamps, needle drivers, towels, sponges, etc.), and to track the movement of those items during a procedure. Then, after a procedure is completed, if one or more of those items which had been detected being placed inside a patient during a procedure was not detected as having been removed once the procedure was complete, an alert could be generated informing the surgeon or other operating room personnel of the issue so that it could be addressed immediately rather than only after some complications developed in the patient.

Figure 22:
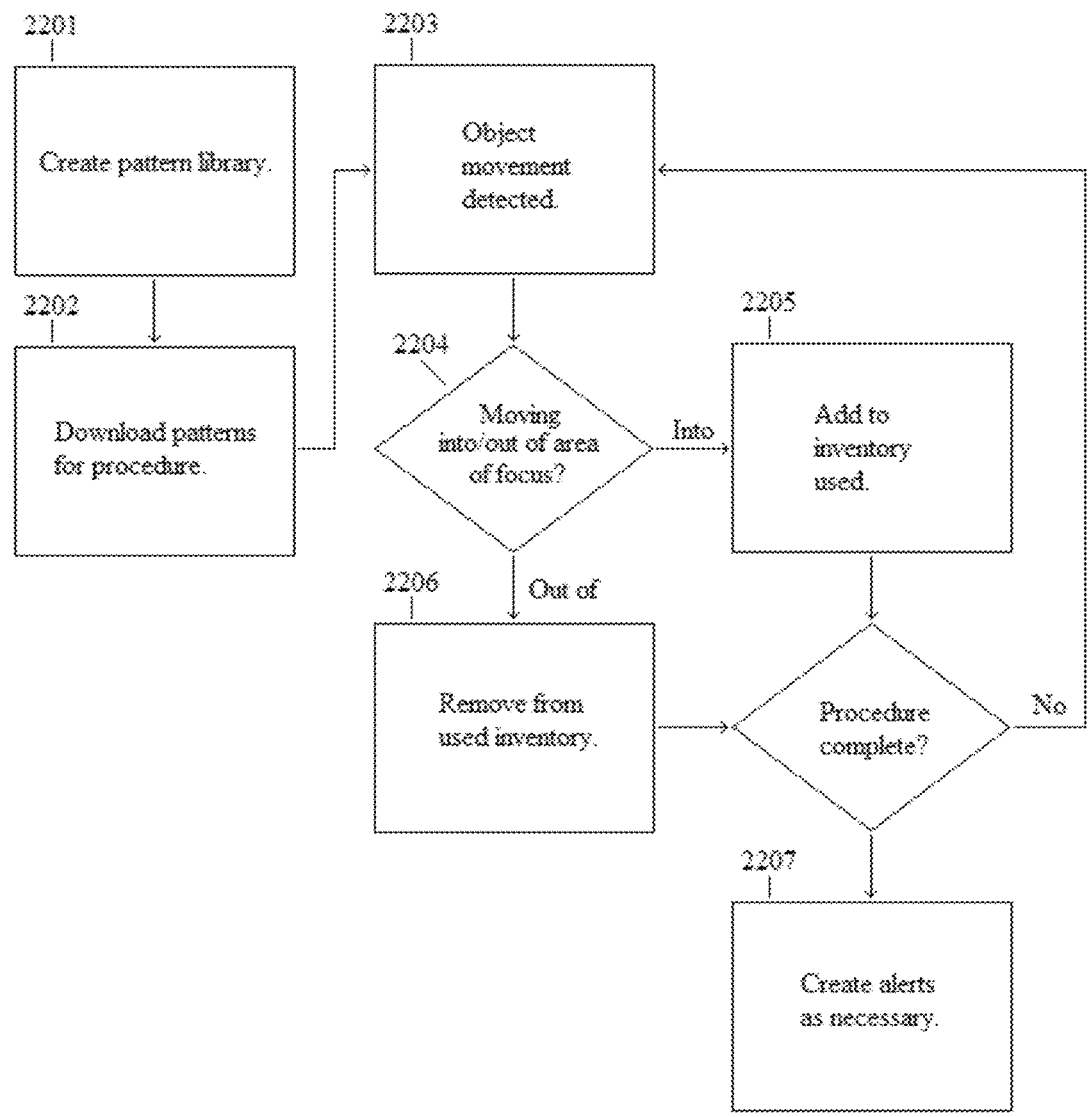
FIG. 22 depicts a method which could be used for surgical inventory management.

To illustrate how object recognition and inventory management such as described in the preceding paragraph could be implemented using the disclosed technology, consider the flowchart of FIG. 22, which depicts a preferred method for such implementation. Initially, in the method of FIG. 22, disposables, instruments and other items to be tracked during surgery are scanned 2201 to create a library of patterns which can be used to recognize objects during a procedure. This can be done, for example, by taking pictures of each item which could be added to a preference card from multiple angles and/or by 3D scanning those items, in order to determine contour information (e.g., a three dimensional shape for the item, an outline for the item, a set of outlines representing the item as seen from multiple angles, etc.) for those items (e.g., as could be represented by a vertex mesh, point cloud or other suitable data structure) which could be stored in the database at the cloud platform. This contour information could also be augmented with character information (e.g., data reflecting the external appearance of particular items, such as barcodes or names which might be printed on them), such as by overlaying meshes representing an objects contours with textures representing its markings, coloring or similar attributes.

After a library of patterns had been created 2201, when a procedure which would use one or more items corresponding to patterns in that library was to take place, the patterns from the library corresponding to the items which would be used in the procedure could be downloaded 2202 to a device which would be present in the operating room during the procedure. This could be done in a manner similar to the downloading of preference card information described previously in the context of FIG. 17. That is, when an individual responsible for preparing an operating room logged in, the system could identify the procedures he or she would be present for using hospital scheduling information, identify the items which would be present using those procedures using previously created preference card information, and then download 2202 the patterns (e.g., contour and/or character information) from the library at the cloud based platform so that they could be accessed during the procedures even if those procedures were performed in a context in which a connection to the cloud based platform was unavailable.

During a procedure, a high resolution video camera array, which would preferably include multiple cameras having overlapping fields of view (e.g., Google glass worn by a surgeon, overhead and various stationary cameras located around the operating room, etc.) to ensure coverage of the entire operating theater, would be used to track the locations of items used in the procedure and to identify when they appeared to enter and leave the procedure's area of focus.

For example, when movement is detected 2203 (e.g., using a threshold frame subtraction and buffer and detection zone algorithm, or other appropriate object recognition algorithm) in an object which matches one of the profiles from the inventory of surgical items, a check 2204 could be made of whether the object is moving into or out of the area of focus of the procedure (e.g., a portion of a patient which is being operated on). Then, if the object is detected moving into the area of focus, a representation of that object could be added 2205 to an inventory used data structure (e.g., a flag representing that object could be flipped) showing that that object was in the area of focus. Similarly, if the object is detected moving out of the area of focus, representation of that object could be removed 2206 from the used inventory data structure (e.g., by flipping a flag back to a null state, etc.).

Ultimately, once the procedure had been completed, the information generated through object recognition as described above could be used to create 2207 any alerts which might be necessary related to the items which had/had not been used. For example, if any objects had been moved into the area but not removed, an alert could be generated notifying operating room personnel that those items may have inadvertently been left inside the patient after the procedure was completed. Other types of alerts might also be generated. For instance, in some embodiments, a list may be maintained indicating which of the items from a preference card were actually used during a procedure, and after the procedure was completed that list could be consulted to determine if any of the items were not used and therefore should potentially be removed from the preference card, thereby reducing cost for the procedure going forward.

Figure 20:
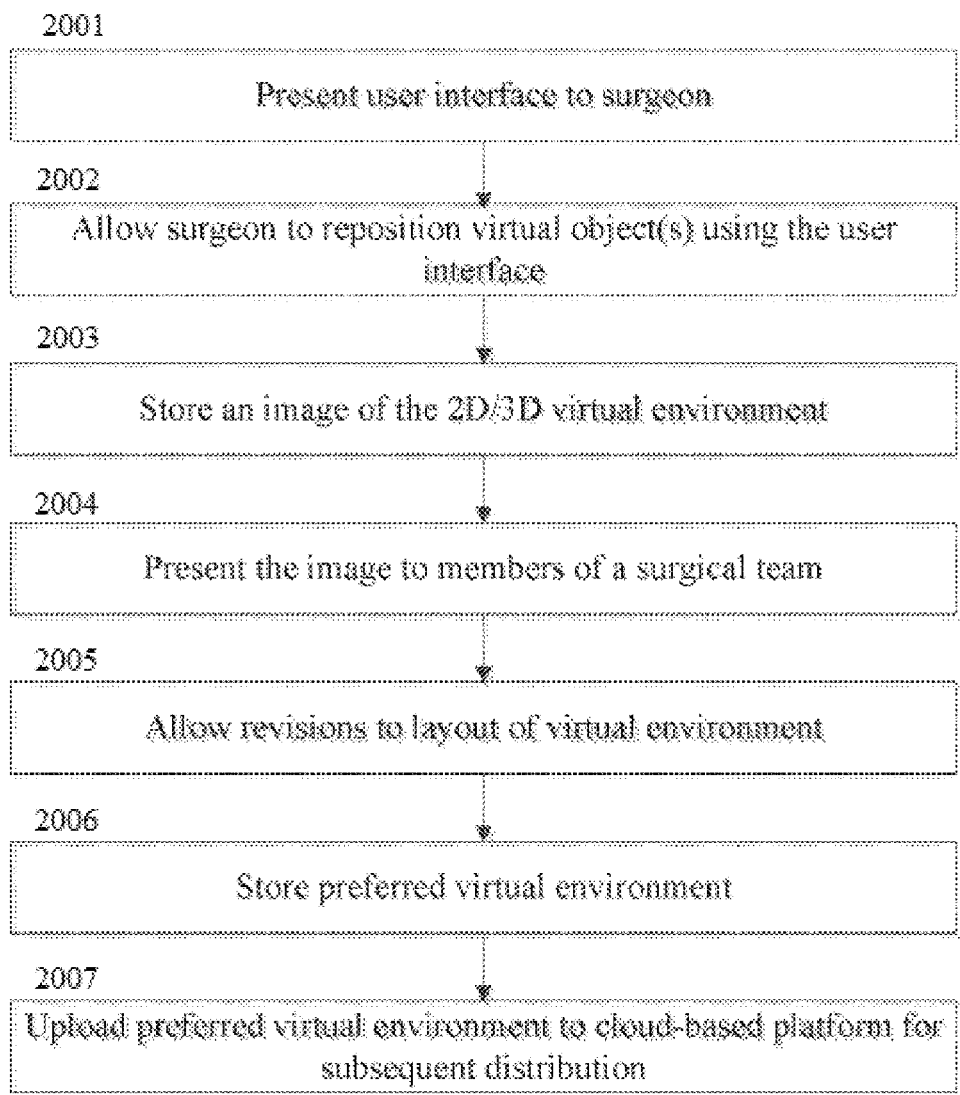
FIG. 20 depicts a method for properly orienting a patient within an operating room prior to a surgical procedure.

To further illustrate how positioning facilitation as described above could be integrated into a process such as described previously, consider FIG. 20, which depicts a method for properly orienting a patient within an operating room prior to a surgical procedure. In the method of FIG. 20, a user interface (e.g., as depicted in FIGS. 7-11) is initially shown to a surgeon that allows the surgeon to manipulate virtual objects in an interactive manner 2001, rather than simply view a passive environment of observed fixed 2D slide images showing surgical procedural details, sequences, positions, personnel, and related resources using the operating room during surgery. The user interface may be accessible, for example, through a mobile application that is executed by the surgeon's mobile phone or through a web browser. Other objects (e.g., carts, people, tools, disposables, oxygen tubes, supplies) may also be moved and repositioned in a 2D or 3D format with the ability to save different versions (e.g., for different operating rooms or different hospitals) and track edits. As discussed previously, the user interface may allow the surgeon to reposition a virtual object in a 2D or 3D environment 2002. For example, a touch-sensitive display may allow the surgeon to drag and drop the virtual object using his/her fingers. Repositioning the virtual object allows the surgeon to specify the optimal patient positioning and/or optimal item positioning. In some embodiments, rather than issuing an abstract command or specifying coordinates and rotation angles, the surgeon may digitally select or "grab" a digital object (e.g., using a button or gesture) and move it around the virtual environment using natural, physical motions.

Additionally or alternatively, in some embodiments, the limbs on a virtual human body may be manipulated via finger swipes or some other gesture to provide greater control over patient positioning. In some embodiments, the physical arm is configured to a small space around the virtual human body of the patient. Consequently, only nearby objects may be selectable, and the area of object movement may be restricted as well. Manipulation techniques may be used to allow the surgeon to move one of the limbs to a position that illustrates the surgeon's preferences for positioning during a specific surgical procedure. In addition to positioning the patient's virtual body on the operating room table, in some embodiments other virtual objects can be grabbed, dragged, and manipulated in the immersive 2D or 3D virtual environment. For example, similar interactions may be used to manipulate other objects that will reside within the operating room, such as surgical team members/staff, carts, trays, etc. These drag-and-drop techniques provide significant advantages in terms of ease of use and efficiency in creating flexible preference cards that take advantage of modern computing capabilities.

As set forth previously, images of the 2D or 3D virtual environment may be stored along with other preference card information input by the surgeon 2003. For example, the images may be stored by the computing device used to access the user interface and/or by a cloud-based platform responsible for creating and supporting the user interface. In some embodiments, the images and/or the preference card information are added to the operating room environment (e.g., shown on the display of a workstation) so the operating room can more easily be configured to be set up in accordance with the surgeon's preferences.

The method of FIG. 20 may also include presenting the visual representation of the operating room content for other surgical team members 2004. Digital elements of the visual representation may be shown in 2D, 3D, or some combination thereof. For instance, in some embodiments 3D digital elements may appear to integrate with 2D digital elements in the same visual representation. One example of this is using a photograph or drawing of the actual operating room and superimposing a 3D human form on the operating room table.

The user interfaces described herein may allow user manipulating of the 3D human form to reposition it in a precise manner to illustrate proper positioning for a particular surgical procedure. Other elements in the operating room (e.g., tubes, wires, and equipment) may be linked to repositioning of the patient so that the surgeon may only need to interact with the 3D human form in order to effect other necessary changes. Revisions to these other elements could be reviewed by other members of the surgical team. Consequently, revisions by the surgeon and/or other members of the surgical team may be allowed 2005. In some embodiments, variations and edits are tracked and stored as different versions of the virtual environment. For example, a cloud-based platform may track which member of the surgical team is responsible for each edit, whether that edit has been approved by the surgeon, etc. Once a revised and edited "preference" for a particular surgeon (and surgical team) for a particular surgery has been finalized, the preferred layout can be saved 2006. The preferred layout may be saved as a screenshot of the virtual environment, as a series of coordinates specifying the desired location of the patient and other item(s), etc. Moreover, the preferred layout may be uploaded to a cloud-based platform using one or more APIs (or other segments of code) to allow for the preferred layout to be more easily shared across multiple computing devices 2007.

It should be understood that, in addition to providing the direct benefits described in the foregoing disclosure, the disclosed technology could indirectly provide benefits through third party applications or devices which could use a system implemented based on this disclosure as, essentially, an operating system for an operating room. For example, just as an operating system will be aware of devices in a computer system, some systems implemented using the disclosed technology could use information from a preference card (potentially combined with information gathered using beacons) to identify the individuals present in an operating room. Similarly, just as an operating system can appropriately route information to and from those devices, the disclosed technology could be used to appropriately route information to various people in an operating room (e.g., if a message is received that should be sent to an OR nurse, the disclosed technology could cause a pop-up notification to appear on a computing device associated with the OR nurse, or could cause a message to be displayed on a screen in the operating room which was identified as being to the attention of the OR nurse), or to react when information was obtained from those individuals (e.g., when it was detected that a stressful event had been experience by the surgeon, a stress event could be generated and recorded in a preference card and/or used to trigger other processing in the same manner as an interrupt would in a conventional computer system).

Additionally (or alternatively) in some cases the disclosed technology could be used to coordinate even with individuals outside of an OR. For example, in some embodiments, software operating on a mobile device in an operating room could be configured (through explicit programming, rules, through practices automatically learned from gathering and analyzing past procedures and interactions with extra-OR stakeholders, etc.) to respond to a tumor being removed from a patient by automatically calling or sending an alert to a pathologist. In such an embodiment, the mobile device could leverage locally stored contacts information to identify the phone number (or other preferred contact method) of a pathologist who would analyze a specimen taken from that tumor and then use that phone number (or other preferred contact method) to automatically notify the pathologist that the tumor was being routed to him or her.

An embodiment of the disclosed technology configured to function as an operating room operating system could do more than route and respond to various communications. For example, just as an operating system can expose application programming interfaces (APIs) to allow interaction with third party applications, the disclosed technology can be used to implement a system which would expose operating room APIs, that third party applications could use to obtain contextual information about a procedure (e.g., what phase the procedure was currently in, which could be determined based on time elapsed, preference card information and/or information from a surgical digital assistant as described previously). Similarly, a system implemented based on the disclosed technology could generate triggers based on actions in a procedure (e.g., the procedure moves from one phase to another, someone enters or leaves the operating room, a particular type of sound is detected, etc.) which third party applications could interact with in much the same way as they would events (e.g., mouse clicks, button presses, etc.) in a conventional computer system. In this way, in addition to directly improving surgical practices, the disclosed technology could provide significant indirect benefits by enabling a platform upon which third party applications could be deployed to achieve objectives even beyond those described herein.

Figure 21:
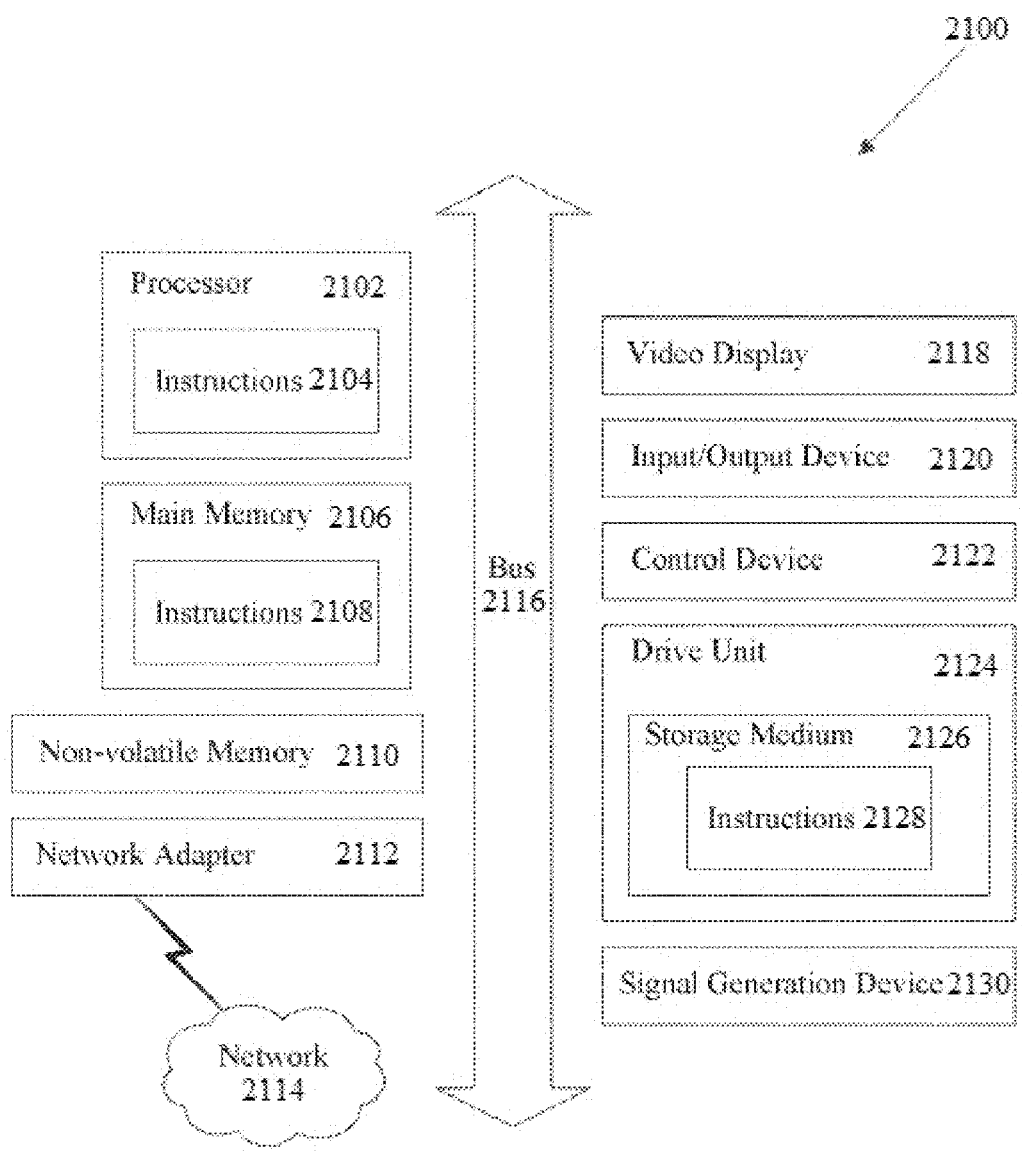
FIG. 21 is a block diagram illustrating an example of a computing system in which at least some operations described herein can be implemented.

FIG. 21 is a block diagram illustrating an example of a computing system 2100 in which at least some operations described herein can be implemented. The computing system may include one or more central processing units ("processors") 2102, main memory 2106, non-volatile memory 2110, network adapter 2112 (e.g., network interfaces), video display 2118, input/output devices 2120, control device 2122 (e.g., keyboard and pointing devices), drive unit 2124 including a storage medium 2126, and signal generation device 2130 that are communicatively connected to a bus 2116. The bus 2116 is illustrated as an abstraction that represents any one or more separate physical buses, point to point connections, or both connected by appropriate bridges, adapters, or controllers. The bus 2116, therefore, can include, for example, a system bus, a Peripheral Component Interconnect (PCI) bus or PCI-Express bus, a Hyper-Transport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the computing system 2100 operates as a standalone device, although the computing system 2100 may be connected (e.g., wired or wirelessly) to other machines. In a networked deployment, the computing system 2100 may operate in the capacity of a server or a client machine in a client-server network environment, or as a peer machine in a peer-to-peer (or distributed) network environment.

The computing system 2100 may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, or any machine capable of executing a set of instructions (sequential or otherwise) that specify actions to be taken by the computing system.

While the main memory 2106, non-volatile memory 2110, and storage medium 2126 (also called a "machine-readable medium) are shown to be a single medium, the term "machine-readable medium" and "storage medium" should be taken to include a single medium or multiple media (e.g., the memory used by platform modules, including: a centralized or distributed database, and/or associated physical memory, device cache, servers, rules engines, code repositories) that store one or more sets of instructions 2128. The term "machine-readable medium" and "storage medium" shall also be taken to include any medium that is capable of storing, encoding, or carrying a set of instructions for execution by the computing system and that cause the computing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 2104, 2108, 2128) set at various times in various memory and storage devices in a computer, and that, when read and executed by one or more processing units or processors 2102, cause the computing system 2100 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 2110, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 2112 enables the computing system 2100 to mediate data in a network 2114 with an entity that is external to the computing device 2100, through any known and/or convenient communications protocol supported by the computing system 2100 and the external entity. The network adapter 2112 can include one or more of a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 2112 can include a firewall which can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

As indicated above, the techniques introduced here implemented by, for example, programmable circuitry (e.g., one or more microprocessors), programmed with software and/or firmware, entirely in special-purpose hardwired (i.e., non-programmable) circuitry, or in a combination or such forms. Special-purpose circuitry can be in the form of, for example, one or more application-specific integrated circuits (ASICs), programmable logic devices (PLDs), field-programmable gate arrays (FPGAs), etc.

Additional variations not explicitly described herein will be immediately apparent to, and could be implemented by those of ordinary skill in the art in light of, this disclosure. Accordingly, instead of limiting the protection accorded by this document, or by any document which is related to this document, to the material explicitly disclosed herein, the protection should be understood to be defined by the following claims, which are drafted to reflect the scope of protection sought by the inventors in this document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to the claims based on the above disclosure or the incorporated priority documents is in any way narrower than the interpretation which would be given based on the "Explicit Definitions" and the broadest reasonable interpretation as provided by a general purpose dictionary, the interpretation provided by the "Explicit Definitions"

and broadest reasonable interpretation as provided by a general purpose dictionary shall control, and the inconsistent usage of terms in the specification or priority documents shall have no effect. Similarly, in the event that one of ordinary skill in the art might, in other contexts, give terms set forth under the heading "Explicit Definitions" meanings different than those set forth under that heading, the interpretations which those of ordinary skill in the art might give those terms in other contexts shall have no effect and the definitions set forth under the heading "Explicit Definitions" shall control.

Explicit Definitions

When used in the claims, a statement that something is "based on" something else should be understood to mean that something is determined at least in part by the thing that it is indicated as being "based on." When something is required to be completely determined by a thing, it will be described as being "based EXCLUSIVELY on" the thing.

When used in the claims, "cache memory" should be understood as random access memory (RAM) that a microprocessor can access more quickly than it can access regular RAM. This memory is typically integrated directly with a CPU chip or placed on a separate chip that has a separate bus interconnected with the CPU.

When used in the claims, "local memory" should be understood as storage elements which are part of the device they are "local" to. These storage elements can include physical memory, cache memory, non-volatile memory, or other types of memory which can be used to store data.

When used in the claims, "means for allowing definition of preferences for a medical procedure" should be understood as a means+function limitation as provided for in 35 U.S.C. § 112(f), in which the function is "allowing definition of preferences for a medical procedure" and the corresponding structure is a computer (which could be a mobile computing device such as a tablet computer) configured to perform processes as described in the context of FIG. 2 (particularly steps 201-210) and FIGS. 3-16.

When used in the claims, "means for automatically tracking surgical inventory items and determining their physical positions in an operating room using a computer vision system" should be understood as a means+function limitation as provided for in 35 U.S.C. § 112(f), in which the function is "automatically tracking surgical inventory items and determining their physical positions in an operating room using a computer vision system" and the corresponding structure is a video camera array and a memory and processor configured to perform processes as described in the context of FIG. 22 (particularly steps 2203-2207).

When used in the claims, "means for ensuring availability of time sensitive information regarding the medical procedure for a user even when the user's device is offline" should be understood as a means+function limitation as provided for in 35 U.S.C. § 112(f) in which the function is "ensuring availability of time sensitive information regarding the medical procedure for a user even when the user's device is offline" and the corresponding structure is a cloud based platform and remote computing device which are configured to coordinate as described in the context of FIG. 17 to perform the specified function.

When used in the claims, "non-volatile memory" should be understood as a type of computer memory from which stored information can be retrieved even after having been power cycled (i.e., turned off and back on). Examples of non-volatile memory include flash memory, ferroelectric ram, magnetic hard disk drives and solid state drives).

When used in the claims, "physical memory" should be understood as referring to RAM chips or modules, typically installed on a computer's motherboard.

When used in the claims, the word "set" should be understood as referring to a number, group or combination of zero or more things of similar nature, design, or function.

When used in the claims, "surgical inventory item" should be understood to refer to a hand tool (e.g., clamp, scissors) or disposable item (e.g., sponge, towel) used directly on or in a patient during a surgical procedure.

What is claimed is:

1. A system comprising:
   a) a cloud based platform comprising a data coordination program;
   b) a set of computing devices, each of which is:
      i) configured with a preference application; and
      ii) located remotely from the cloud based platform;
   wherein:
   A) for each of the computing devices in the set of computing devices, the preference application configures that computing device to:
      I) send login information for a user of that device to the cloud based platform;
      II) present a set of preference definition interfaces to the user of that device wherein the set of preference definition interfaces comprises a set of patient position images selectable via the preference application;
      III) send, to the cloud based platform, preferences for a medical procedure specified using the set of preference definition interfaces, along with metadata indicating:
         a) the medical procedure for which those preferences were specified; and
         b) the user to whom the set of preference definition interfaces was presented when those preferences were specified for the medical procedure;
      IV) store, in local memory on that computing device, data received from the cloud based platform as connectivity invariant accessible data; and
      V) based on a request for data received from the cloud based platform as connectivity invariant accessible data:
         a) in the event a connection to the cloud based platform is available, retrieve and present the requested data from the cloud based platform;
         b) in the event a connection to the cloud based platform is not available, retrieve and present the requested data from the local memory of the computing device;
   B) the data coordination program comprises instructions operable to, when executed, cause a computer used to host the cloud based platform to:
      I) store preferences received from computing devices with associated metadata in a central database; and
      II) based on login information received from a computing device:
         a) determining information to be made accessible to the user of that computing device during a future time period; and
         b) sending, from the central database, the information determined to be made available to the user of that computing device during the future time period as connectivity invariant accessible data;
   C) the set of patient position images comprises:
      I) a supine position image;

II) a prone position image; and
III) a lateral position image;
D) the prone position image is a prone arm down image;
E) the set of patient position images further comprises a prone arm up image;
F) the supine position image is a supine arm down image;
G) the set of patient images comprises a supine unilateral arm up image;
H) the set of patient images comprises a supine bilateral arm up image; and
I) the set of patient images comprises a supine legs spread image.

2. The system of claim 1, wherein:
a) the set of preference definition interfaces comprises:
   i) a graphical depiction of an operating room;
   ii) a set of cart images; and
   iii) a set of personnel images;
b) the set of cart images and the set of personnel images are selectable via the preference application;
c) the preference application is configured to populate the graphical depiction of the operating room with:
   i) a patient position image corresponding to an image selected from the set of patient position images;
   ii) one or more cart images corresponding to at least one cart image selected from the set of cart images;
   iii) one or more images of personnel corresponding to at least one personnel image selected from the set of personnel images; and
d) the preference application is configured to allow images which populate the graphical depiction of the operating room to be repositioned, and to include positioning of the images which populate the graphical depiction of the operating room as preference information for the medical procedure specified using the set of preference definition interfaces.

3. The system of claim 2, wherein the graphical depiction of an operating room is selected from a group consisting of:
a) a 2D depiction of the operating room; and
b) a 3D depiction of the operating room.

4. The system of claim 2, wherein the positioning of the images which populate the graphical depiction of the operating room is represented as percentage offsets for the items in a display.

5. The system of claim 2, wherein:
a) the set of preference definition interfaces comprises an interface operable to display a photograph of a cart for selection by a user; and
b) each of the one or more cart images the preference application is configured to populate the graphical depiction of the operating room with is a non-photographic icon.

6. The system of claim 1, wherein the preference application comprises instructions configured to, when executed, cause display of a set of phases of a medical procedure.

7. The system of claim 6, wherein the preference application comprises instructions operable to allow a user of the preference application to define preferences for a primary medical procedure by performing acts comprising indicating that a secondary medical procedure should be incorporated as a phase of the primary medical procedure.

8. The system of claim 1, wherein the data coordination application comprises instructions to:
a) receive a publication signal indicating that a set of preferences defined for a medical procedure should be published at a medical institution;
b) based on receiving the publication signal, evaluate one or more rules to determine a set of approvals necessary for publication of the set of preferences at the medical institution; and
c) for each approval in the set of approvals, generate a request for the set of preferences to be approved for publication.

9. The system of claim 8, wherein the one or more rules are selected from a group consisting of:
a) a set of rules which are specific to the medical institution; and
b) a set of default rules.

10. The system of claim 1, wherein the set of preference definition interfaces is operable by the user to specify one or more risk mitigations associated with a selected patient position image, wherein the one or more risk mitigations comprises:
a) a cushion;
b) an arm board;
c) a heating pad; and
d) a cooling pad.

11. The system of claim 1, wherein:
a) the cloud based platform is configured to, for each of a plurality of medical procedures, derive a set of best practices for that medical procedure based on preference information specified for that medical procedure using preference definition interfaces presented on the computing devices from the set of computing devices; and
b) for each computing device from the set of computing devices, the preference application configures that computing device to:
   i) determine if a corresponding best practice exists based on determining that the user of that device is specifying a preference for a medical procedure having a corresponding best practice comprised by the set of best practices for that medical procedure; and
   ii) in the event that it is determined that the corresponding best practice exists, provide the user a notification of the corresponding best practice.

12. A system comprising:
a) a cloud based platform comprising a data coordination program;
b) a set of computing devices, each of which is:
   i) configured with a preference application; and
   ii) located remotely from the cloud based platform;
wherein:
A) for each of the computing devices in the set of computing devices, the preference application configures that computing device to:
   I) send login information for a user of that device to the cloud based platform;
   II) present a set of preference definition interfaces to the user of that device wherein the set of preference definition interfaces comprises a set of patient position images selectable via the preference application;
   III) send, to the cloud based platform, preferences for a medical procedure specified using the set of preference definition interfaces, along with metadata indicating:
      a) the medical procedure for which those preferences were specified; and
      b) the user to whom the set of preference definition interfaces was presented when those preferences were specified for the medical procedure;

IV) store, in local memory on that computing device, data received from the cloud based platform as connectivity invariant accessible data; and V) based on a request for data received from the cloud based platform as connectivity invariant accessible data:
   a) in the event a connection to the cloud based platform is available, retrieve and present the requested data from the cloud based platform;
   b) in the event a connection to the cloud based platform is not available, retrieve and present the requested data from the local memory of the computing device;

B) the data coordination program comprises instructions operable to, when executed, cause a computer used to host the cloud based platform to:
   I) store preferences received from computing devices with associated metadata in a central database; and
   II) based on login information received from a computing device:
      a) determining information to be made accessible to the user of that computing device during a future time period; and
      b) sending, from the central database, the information determined to be made available to the user of that computing device during the future time period as connectivity invariant accessible data; and C) the set of preference definition interfaces is operable by the user to specify one or more risk mitigations associated with a selected patient position image, wherein the one or more risk mitigations comprises:
   I) a cushion;
   II) an arm board;
   III) a heating pad; and
   IV) a cooling pad.

13. A system comprising:
a) a cloud based platform comprising a data coordination program;
b) a set of computing devices, each of which is:
   i) configured with a preference application; and
   ii) located remotely from the cloud based platform;
wherein:
A) for each of the computing devices in the set of computing devices, the preference application configures that computing device to:
   I) send login information for a user of that device to the cloud based platform;
   II) present a set of preference definition interfaces to the user of that device wherein the set of preference definition interfaces comprises a set of patient position images selectable via the preference application;
   III) send, to the cloud based platform, preferences for a medical procedure specified using the set of preference definition interfaces, along with metadata indicating:
      a) the medical procedure for which those preferences were specified; and
      b) the user to whom the set of preference definition interfaces was presented when those preferences were specified for the medical procedure;
   IV) store, in local memory on that computing device, data received from the cloud based platform as connectivity invariant accessible data; and
   V) based on a request for data received from the cloud based platform as connectivity invariant accessible data:
      a) in the event a connection to the cloud based platform is available, retrieve and present the requested data from the cloud based platform;
      b) in the event a connection to the cloud based platform is not available, retrieve and present the requested data from the local memory of the computing device;
B) the data coordination program comprises instructions operable to, when executed, cause a computer used to host the cloud based platform to:
   I) store preferences received from computing devices with associated metadata in a central database; and
   II) based on login information received from a computing device:
      a) determining information to be made accessible to the user of that computing device during a future time period; and
      b) sending, from the central database, the information determined to be made available to the user of that computing device during the future time period as connectivity invariant accessible data;
C) the cloud based platform is configured to, for each of a plurality of medical procedures, derive a set of best practices for that medical procedure based on preference information specified for that medical procedure using preference definition interfaces presented on the computing devices from the set of computing devices; and
D) for each computing device from the set of computing devices, the preference application configures that computing device to:
   I) determine if a corresponding best practice exists based on determining that the user of that device is specifying a preference for a medical procedure having a corresponding best practice comprised by the set of best practices for that medical procedure; and
   II) in the event that it is determined that the corresponding best practice exists, provide the user a notification of the corresponding best practice.

* * * * *